(12) United States Patent
Bosua

(10) Patent No.: US 11,628,234 B2
(45) Date of Patent: Apr. 18, 2023

(54) WHITE LIGHT LED LIGHT BULBS FOR AMBIENT LIGHTING AND PATHOGEN INACTIVATION

(71) Applicant: Know Labs, Inc., Seattle, WA (US)

(72) Inventor: Phillip Bosua, Seattle, WA (US)

(73) Assignee: KNOW LABS, INC., Seattle, WA (US)

( * ) Notice: Subject to any disclaimer, the term of this patent is extended or adjusted under 35 U.S.C. 154(b) by 77 days.

(21) Appl. No.: 17/209,960

(22) Filed: Mar. 23, 2021

(65) Prior Publication Data

US 2021/0369905 A1  Dec. 2, 2021

Related U.S. Application Data

(60) Provisional application No. 63/074,720, filed on Sep. 4, 2020, provisional application No. 63/032,969, filed on
(Continued)

(51) Int. Cl.
*A61L 9/20* (2006.01)
*F21K 9/238* (2016.01)
(Continued)

(52) U.S. Cl.
CPC ............... *A61L 9/20* (2013.01); *F21K 9/238* (2016.08); *H05B 47/125* (2020.01); *H05B 47/17* (2020.01);
(Continued)

(58) Field of Classification Search
CPC .. A61L 9/20; A61L 2209/111; A61L 2209/12; A61L 2202/11; A61L 2202/14;
(Continued)

(56) References Cited

U.S. PATENT DOCUMENTS 3,670,193 A  6/1972  Thorington et al.
3,875,456 A  4/1975  Kano et al.
(Continued)

FOREIGN PATENT DOCUMENTS

KR  101346576 B1 *  1/2014
KR  101346576 B1     1/2014
(Continued)

OTHER PUBLICATIONS

Machine Translation of KR20190021766A (Year: 2019).*
(Continued)

*Primary Examiner* — Raymond R Chai
(74) *Attorney, Agent, or Firm* — Hamre, Schumann, Mueller & Larson, P.C.

(57) ABSTRACT

Consumable and replaceable light bulbs that emit white light to provide ambient lighting and also emit UV light for pathogen inactivation. The white light and the UV light may be emitted simultaneously or the light bulb can be controlled to emit the white light and the UV light at separate times. The UV light emitted by the light bulbs has a wavelength and output power that is safe for humans and pets and the UV light inactivates pathogens over relatively prolonged exposure periods. The light bulbs described herein can be used in place of conventional light bulbs, for example in a room of a home, office building or other human occupied space. Humans can remain in the space when the light bulb(s) is on without being harmed by the UV light.

45 Claims, 21 Drawing Sheets

Related U.S. Application Data on Jun. 1, 2020, provisional application No. 63/032,965, filed on Jun. 1, 2020, provisional application No. 63/032,981, filed on Jun. 1, 2020.

(51) Int. Cl.
*H05B 47/125* (2020.01)
*H05B 47/19* (2020.01)
*H05B 47/17* (2020.01)

(52) U.S. Cl.
CPC ......... *H05B 47/19* (2020.01); *A61L 2209/111* (2013.01); *A61L 2209/12* (2013.01)

(58) Field of Classification Search
CPC ........ A61L 2202/25; A61L 2/10; F21K 9/238; F21K 9/233; H05B 47/125; H05B 47/17; H05B 47/19; H05B 47/105; H05B 47/115; H05B 45/20; Y02B 20/40; F21V 9/00; F21V 23/045; F21V 23/0471; F21Y 2103/33; F21Y 2115/10
See application file for complete search history.

(56) References Cited

U.S. PATENT DOCUMENTS

| | | |
|---|---|---|
| 3,926,556 A | 12/1975 | Boucher |
| 5,813,753 A | 9/1998 | Vriens et al. |
| 5,847,507 A | 12/1998 | Butterworth et al. |
| 5,887,965 A | 3/1999 | Edens et al. |
| 6,084,250 A | 7/2000 | Jüstel et al. |
| 6,234,648 B1 | 5/2001 | Börner et al. |
| 6,294,800 B1 | 9/2001 | Duggal et al. |
| 6,340,824 B1 | 1/2002 | Komoto et al. |
| 6,357,889 B1 | 3/2002 | Duggal et al. |
| 6,504,301 B1 | 1/2003 | Lowery |
| 6,509,651 B1 | 1/2003 | Matsubara et al. |
| 6,600,175 B1 | 7/2003 | Baretz et al. |
| 6,621,211 B1 | 9/2003 | Srivastava et al. |
| 6,685,852 B2 | 2/2004 | Setlur et al. |
| 6,734,465 B1 | 5/2004 | Taskar et al. |
| 6,791,259 B1 | 9/2004 | Stokes et al. |
| 6,939,481 B2 | 9/2005 | Srivastava et al. |
| 7,824,065 B2 | 11/2010 | Maxik |
| 7,845,825 B2 | 12/2010 | Ramer et al. |
| 7,996,173 B2 | 8/2011 | Schowengerdt et al. |
| 8,039,785 B2 | 10/2011 | Olson et al. |
| 8,076,630 B2 | 12/2011 | Schowengerdt et al. |
| 8,081,304 B2 | 12/2011 | Furness, III et al. |
| 8,285,510 B2 | 10/2012 | Schowengerdt et al. |
| 8,368,878 B2 | 2/2013 | Furness, III et al. |
| 8,398,264 B2 | 3/2013 | Anderson et al. |
| 8,502,247 B2 | 8/2013 | Baretz et al. |
| 8,583,394 B2 | 11/2013 | Schowengerdt et al. |
| 8,779,455 B2 | 7/2014 | Sakuta et al. |
| 8,829,780 B2 | 9/2014 | Sakuta et al. |
| 8,888,207 B2 | 11/2014 | Furness, III et al. |
| 8,988,666 B2 | 3/2015 | Furness, III et al. |
| 9,039,966 B2 | 5/2015 | Anderson et al. |
| 9,041,920 B2 | 5/2015 | Mander et al. |
| 9,046,227 B2 | 6/2015 | David et al. |
| 9,210,779 B2 | 12/2015 | Bosua et al. |
| 9,283,292 B2 | 3/2016 | Kretschmann |
| 9,316,581 B2 | 4/2016 | Mander et al. |
| 9,333,274 B2 | 5/2016 | Peterson et al. |
| 9,368,695 B2 | 6/2016 | David et al. |
| 9,439,989 B2 | 9/2016 | Lalicki et al. |
| 9,625,371 B2 | 4/2017 | Furness, III et al. |
| 9,664,610 B2 | 5/2017 | Mander et al. |
| 9,713,223 B2 | 7/2017 | Barron et al. |
| 9,869,636 B2 | 1/2018 | Mander et al. |
| 9,927,097 B2 | 3/2018 | Lalicki et al. |
| 9,937,274 B2 | 4/2018 | Clynne et al. |
| 9,981,052 B2 | 5/2018 | Clynne et al. |
| 9,987,499 B2 | 6/2018 | Hayashi et al. |
| 10,309,587 B2 | 6/2019 | Aanegola et al. |
| 10,309,614 B1 | 6/2019 | Jones et al. |
| 10,357,582 B1 | 7/2019 | Barron et al. |
| 10,363,327 B2 | 7/2019 | Liao et al. |
| 10,364,944 B2 | 7/2019 | Van Bommel et al. |
| 10,413,626 B1 | 9/2019 | Barron et al. |
| 10,617,774 B2 | 4/2020 | Winslow et al. |
| 10,617,775 B2 | 4/2020 | Hawkins et al. |
| 10,632,214 B2 | 4/2020 | David et al. |
| 2005/0199902 A1* | 9/2005 | Trigiani ................ G01N 21/91 257/103 |
| 2008/0008620 A1 | 1/2008 | Alexiadis |
| 2010/0232135 A1 | 9/2010 | Munehiro et al. |
| 2011/0210273 A1 | 9/2011 | Kurt et al. |
| 2012/0320607 A1 | 12/2012 | Kinomoto et al. |
| 2014/0328046 A1 | 11/2014 | Aanegola et al. |
| 2016/0169498 A1 | 6/2016 | Lei et al. |
| 2016/0334341 A1* | 11/2016 | Moore ................ G01N 21/94 |
| 2017/0359885 A1* | 12/2017 | Roosli ................ H05B 47/19 |
| 2018/0147417 A1 | 5/2018 | Rantala |
| 2018/0180253 A1 | 6/2018 | Lalicki et al. |
| 2018/0185527 A1 | 7/2018 | Lalicki et al. |
| 2018/0185533 A1 | 7/2018 | Lalicki et al. |
| 2018/0209609 A1* | 7/2018 | Hikmet ................ F21K 9/62 |
| 2019/0167825 A1 | 6/2019 | Jones et al. |
| 2019/0298870 A1 | 10/2019 | Barron et al. |
| 2019/0321501 A1 | 10/2019 | Barron et al. |
| 2019/0388572 A1* | 12/2019 | Cole ................ A61N 5/0624 |
| 2020/0016288 A1 | 1/2020 | Lalicki et al. |
| 2020/0038542 A1 | 2/2020 | Franklin et al. |
| 2020/0061222 A1 | 2/2020 | Ukawa et al. |
| 2020/0100491 A1 | 4/2020 | Winslow et al. |
| 2020/0105983 A1 | 4/2020 | Lim et al. |

FOREIGN PATENT DOCUMENTS

| | | | |
|---|---|---|---|
| KR | 20160133863 A | * | 11/2016 |
| KR | 20190021766 | | 3/2019 |
| KR | 20190021766 A | * | 3/2019 |
| KR | 20190065580 | | 6/2019 |
| WO | 9748138 A3 | | 2/1998 |
| WO | 2018080805 | | 5/2018 |
| WO | 2019231834 | | 12/2019 |

OTHER PUBLICATIONS

Machine Translation of KR101346576B1 (Year: 2014).*
Machine Translation of KR20160133863A (Year: 2016).*
International Search Report and Written Opinion issued for International Patent Application No. PCT/IB2021/054126, dated Aug. 17, 2021, 9 pages.
Livingston, S. et al., "Thinking outside the spectrum: Efficacy of a UV-A lighting system for passive disinfection of healthcare associated pathogens," SHEA Spring Conference; Apr. 18-20, 2018 (1 page).
"Current's 365DisInFx™ Technology—The ideal germicidal UV solution for any occupied space," Brochure, GE current, a Daintree company, Loeb Electric, © 2020 Current Lighting Solutions, LLC. {6 pages).
"The Efficacy of 405nm Antibacterial LED Light—Highlights From Six Studies in Multiple Settings," vital vio, © 2019 Vital Vio, Inc. (16 pages).
Vital vio Product Portfolio, Mar. 20 (11 pages).
Kvam, E. et al., "Mechanistic insights into UV-A mediated bacterial disinfection via endogenous photosensitizers," Journal of Photochemistry & Photobiology, B: Biology 209 (2020) 111899 (10 pages).
U.S. Appl. No. 29/773,613, titled "LED Bulb," filed Mar. 10, 2021 (5 pages).
U.S. Appl. No. 29/773,614, titled "LED Bulb," filed Mar. 10, 2021 (3 pages).
U.S. Appl. No. 29/773,617, titled "LED Bulb," filed Mar. 10, 2021 (4 pages).

* cited by examiner

WHITE LIGHT LED LIGHT BULBS FOR AMBIENT LIGHTING AND PATHOGEN INACTIVATION

PRIORITY

This application claims the benefit of U.S. Provisional Application Ser. No. 63/032,965, Ser. No. 63/032,969, Ser. No. 63/032,981, and Ser. No. 63/074,720, each of which is incorporated herein by reference in its entirety.

FIELD

This technical disclosure relates to light bulbs that can be used for both ambient lighting in a room and inactivating pathogens, such as bacteria and viruses, in the room using ultraviolet (UV) light.

BACKGROUND

The use of UV light to inactivate pathogens, such as bacteria and viruses, is well known. In many conventional systems that rely on UV light to inactivate pathogens, the UV light is operated at shorter wavelengths in powerful pulses to inactivate the pathogens as quickly as possible. However, the UV light in these systems is harmful to humans and therefore humans cannot be present during operation of these systems or special precautions need to be implemented to protect any humans that are present from the UV light.

SUMMARY

Apparatus, systems and methods are described herein that involve the use of consumable and replaceable light bulbs that can emit white light to provide ambient lighting and also emit UV light for pathogen inactivation. The white light and the UV light may be emitted simultaneously or the light bulb can be controlled to emit the white light and the UV light at separate times. The light bulbs described herein may also be referred to as light emitting devices or electric lamps. In one embodiment, the UV light emitted by the light bulbs can have a wavelength and output power that is considered safe for humans and pets and the UV light inactivates pathogens over relatively prolonged exposure periods. For example, the bulb is a human safe UV-A spectrum hybrid bulb that is compliant with the IEC 62471 International Photobiological Safety standard. The light bulbs described herein can be used in place of conventional light bulbs, for example in a room of a home, office building or other human occupied space. Humans can remain in the space when the light bulb(s) is on and emitting UV light without being harmed by the UV light. In another embodiment, the light bulb can emit UV light which may be considered as being harmful to humans or pets. For example, the UV light can be emitted when a human or pet are not present in a room where the light bulb is operating.

In one embodiment described herein, the light bulb can have a form factor that is similar to conventional LED and incandescent light bulbs where the light bulb has a screw-thread base that screws into a threaded socket. This permits the light bulb described herein to be used in place of conventional LED and incandescent light bulbs in a room. However, in some embodiments, the light bulb need not include a screw-thread base and other forms of light bulb mounting and electrical connection can be used.

In some embodiments, the light bulb may be configured as a smart light bulb that is configured to wirelessly communicate with one or more external devices including, but not limited to, a mobile device such as a mobile phone or a tablet computer, or a pathogen sensor. In some embodiments, a plurality of the light bulbs may be provided and the light bulbs may communicate directly or indirectly with one another.

In an example implementation of a light bulb described herein, one or more conventional screw-in light bulbs in a room of a human occupied space are replaced by the light bulbs described herein. The human occupied space can be, but is not limited to, one or more rooms in a house, one or more rooms in an office building, or the like. The light bulb can be activated in conventional manner, for example via a wall switch, to provide illumination in the space. At the same time as providing white light for illumination, the light bulb may emit UV light. In some embodiments, the light bulb may be controlled to emit only white light at certain times, or emit only UV light at certain times.

In one embodiment, the UV light emitted by the light bulb(s) has a wavelength and an output power that is not considered harmful to humans or pets and is sufficient to inactivate pathogens in the space that are exposed to the UV light over a relatively long time period measured in multiple minutes. For example, the exposure time period required for the UV light emitted by the light bulb(s) to inactivate the pathogens can be a minimum of about 10 minutes, or a minimum of about 20 minutes, or a minimum of about 30 minutes, and the like. In addition, the UV light emitted by the light bulb is safe for continuous human exposure at a distance of at least 1 meter for at least 2 hours, and the UV light has a wavelength and a power whereby pathogens located at least 1 meter from the light bulb that are continually exposed to the UV light for at least 2 hours are inactivated. In another embodiment, the UV light emitted by the light bulb is safe for continuous human exposure at a distance of at least 1 meter for at least 8 hours, or for at least 24 hours.

In one embodiment described herein, a light bulb can include a housing and a screw-thread base attached to the housing for threading the light bulb into a threaded socket, where the housing and the screw-thread base define an interior space. A plurality of white light emitting diodes (LEDs) are in the interior space and emit white light. In addition, a plurality of blue LEDs are in the interior space and emit ultraviolet (UV) light. A visible wavelength filter is positioned relative to the blue LEDs to filter out visible wavelengths of the UV light emitted by the blue LEDs.

In another embodiment described herein, a light bulb can include a housing and a screw-thread base attached to the housing for threading the light bulb into a threaded socket, where the housing and the screw-thread base define an interior space. A plurality of white LEDs are in the interior space and emit white light. In addition, a plurality of blue LEDs are in the interior space and emit UV light. The light bulb is devoid of phosphor through which UV light emitted by any one or more of the blue LEDs passes for converting the energy in the emitted UV light to a visible light (also referred to herein as conditioning the UV light). However, in an embodiment, phosphor can be included in the visible wavelength filter to form an external UV light indicator where the phosphor is excitable by the UV light to fluoresce and thereby externally indicate when fluorescing that any one or more of the blue light emitting diodes are emitting UV light.

In another embodiment described herein, a light bulb described herein can be controlled to have various operational modes where the white LEDs and the blue LEDs are controlled to be on or off depending upon data from a motion sensor and/or a distance sensor incorporated into the light bulb.

DRAWINGS

DETAILED DESCRIPTION

Figure 1:
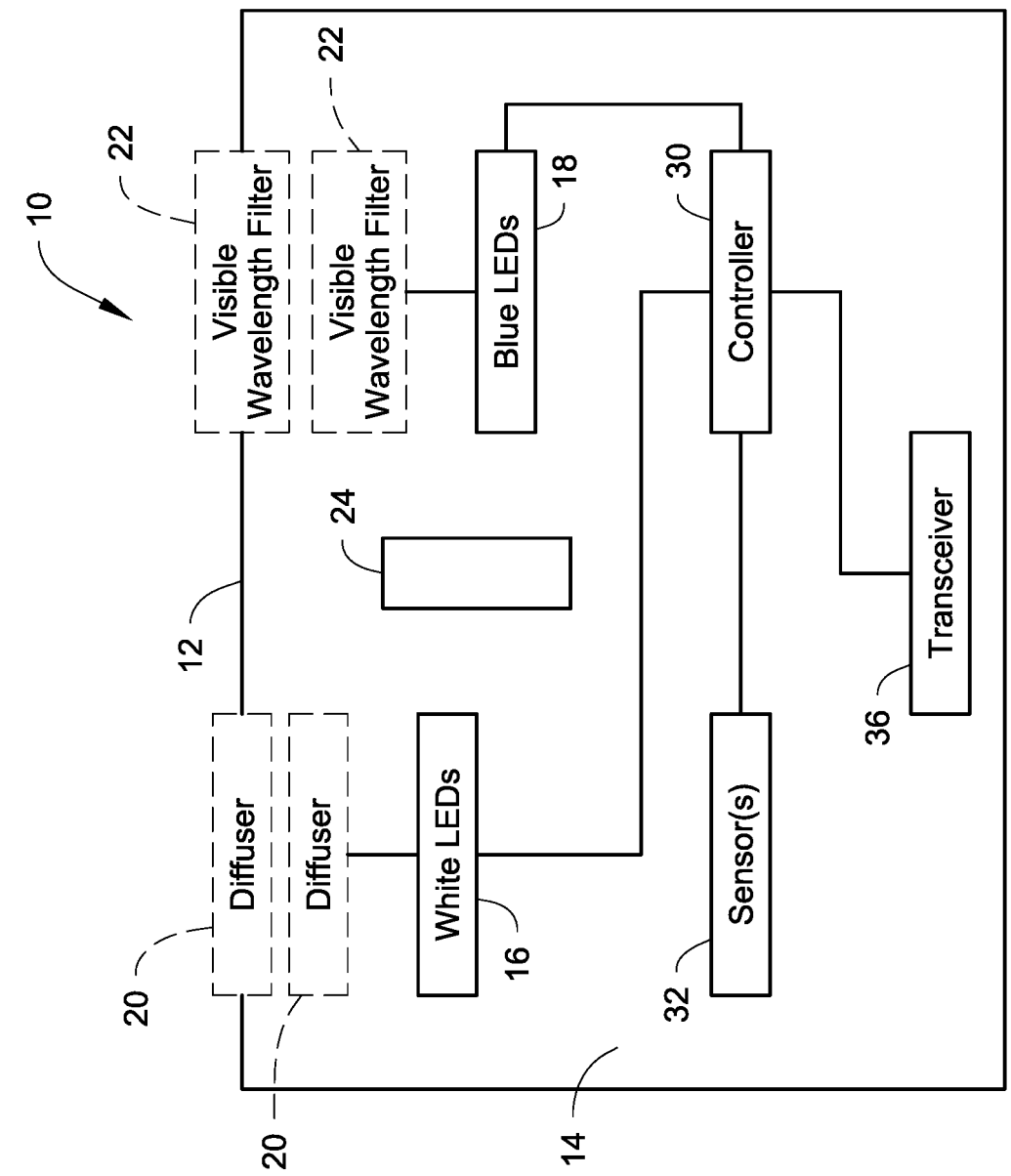
FIG. 1 is a schematic depiction of an embodiment of a light bulb described herein.
Figure 2:
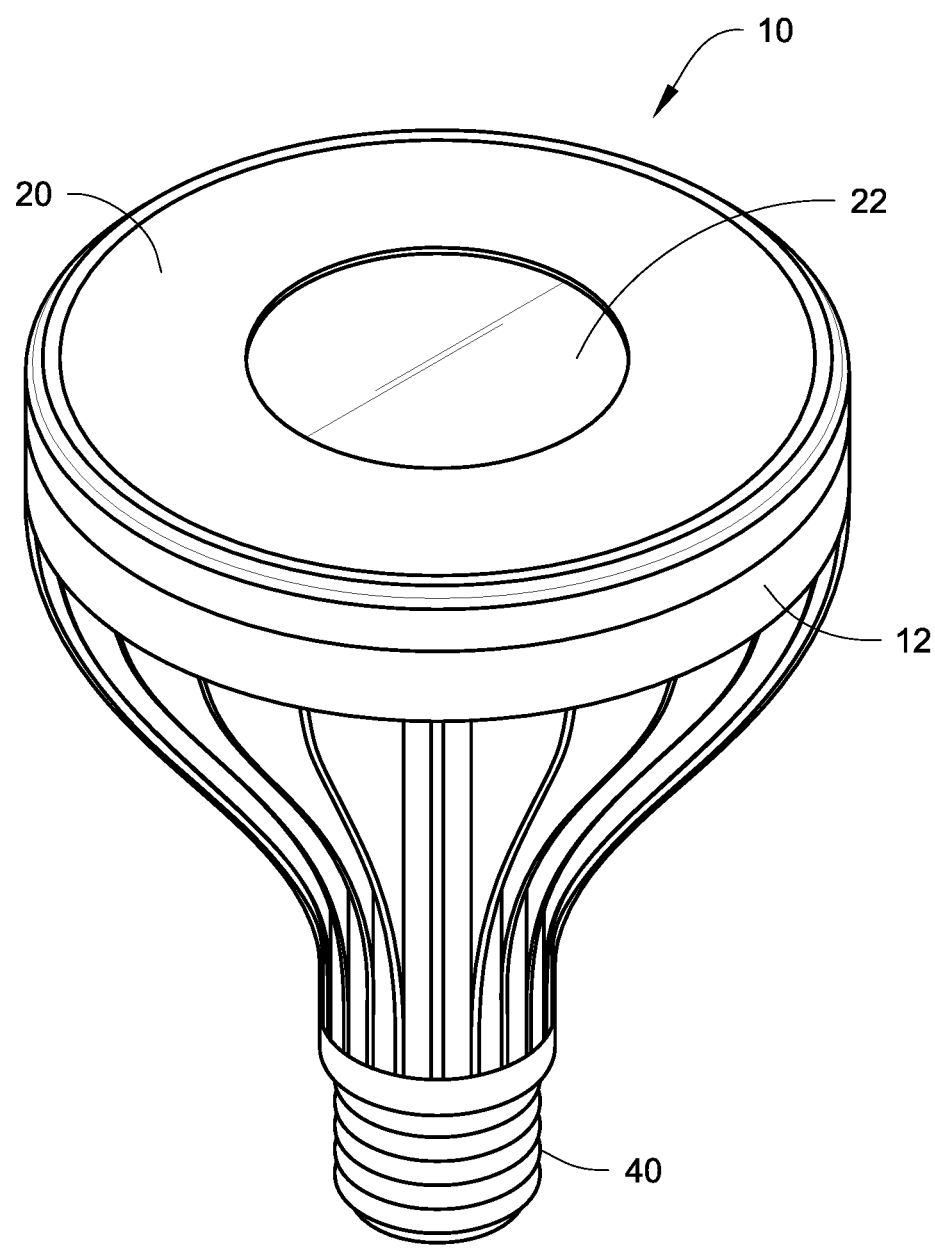
FIG. 2 is a perspective view of an embodiment of a light bulb described herein.

The following is a description of light bulbs that can emit white light to provide ambient lighting and that can also emit UV light for pathogen inactivation. In an embodiment, the white light and the UV light can be emitted simultaneously. In another embodiment, the white light can be emitted while the UV light is not emitted. In another embodiment, the UV light is emitted and the white light is not emitted.

The UV light emitted by the light bulbs is safe for humans and pets during normal use of the light bulbs and the UV light has a wavelength and an output power that is sufficient to inactivate pathogens over relatively prolonged exposure periods. The light bulbs can be used in place of conventional light bulbs, for example in a room of a home, office building or other human occupied spaces. Humans and pets can remain in the space when the light bulb(s) is on and emitting UV light without being harmed by the UV light. In one embodiment, the light bulbs are human safe UV-A spectrum hybrid bulbs that are compliant with the IEC 62471 International Photobiological Safety standard.

The light bulbs can have a form factor that is similar to conventional LED and incandescent light bulbs where the light bulb has a screw-thread base that screws into a threaded socket. This permits the light bulbs described herein to be used in place of conventional LED and incandescent light bulbs in a room. However, in some embodiments, the light bulbs need not include a screw-thread base and other forms of light bulb mounting and electrical connection can be used.

The pathogens that can be inactivated by the UV light include bacteria and viruses. The bacteria can be *Coccus, Bacillus, Spirillum, Rickettsia,* and *Mycoplasma*. Examples of *Coccus* bacteria include, but are not limited to: Staph aureus; S. epidermidis; S. saphrophyticus; S. haemolyticus; S. hominis; S. capitis; S. schleiferi; S. warneri; S. lugdenenis; Strep pyrogenes (gr. A); S. agalactiae (gr. B); E. faecalis; E. faecium; S. pneumonia; S. mutans group; S. salivarus group; S. sanguis group; S. mitis group; S. angiosus group; A. adiacens; S. milleri; S. bovis; N. gonorrhea; N. meningitides; Moraxella catarrhalis. Examples of *Bacillus* bacteria include, but are not limited to: C. diptheriae; C. jeikenium; C. urealyticum; Lactobacillus sp.; Bacillus anthracis; B. cereus; Listeria monocytogenes; Erisipelothrix rhusiopathiae; Arcanobacterium bemolyticum; Escherichia coli; Klebsiella pneumonia; Proteus spp.; Morganella; Providencia; C. freundii; C. koseri; Enterobacter cloacae; E. aerogenes; S. marcecescens; Vibrio cholera; V. parahaemolyticus; V. vulificans; Aeromonas hydrophila; Plesiomonas shigelloides; Stenotrophomonas maltophilia. Examples of *Spirillum* bacteria include, but are not limited to: Treponema pallidum; Treponema carateum; Treponema denticola; Borrelia burgdorferi; Borrelia afzelii; Borrelia hermsii; Borrelia duttoni; Borrelia parkeri; Borrelia recurrentis; Leptospira interrogans; Spirillum minus; Chlamydophila psittaci; Chlamydophila pneumonia; Chlamydia trachomatis; Bacteroides fragilis; Bacteroides forsythus; Capnocytophaga canimorsus; Porphyromonas gingivalis; Prevotella intermedia; Fusobacterium necrophorum; Fusobacterium nucleatum; Fusobacterium polymorphum; Streptobacillus moniliformis. Examples of *Rickettsia* bacteria include, but are not limited to: Rickettsia; Rickettsia akari; Rickettsia conorii; Rickettsia sibirica; Rickettsia australis; Rickettsia felis; Rickettsia japonica; Rickettsia africae; Rickettsia hoogstraalii; Rickettsia prowazekii; Rickettsia typhi. Examples of *Mycoplasma* bacteria include, but are not limited to: M. tuberculosis; M. buccale; M. faucium; M. fermentans; M. gallisepticum; M. genitalium; M. haemofelis; M. hominis; M. hyopneumoniae; M. hyorhinis; M. incognitus; M. lipophilum; M. ovipneumoniae; M. penetrans; M. pirum; M. pneumonia; M. salivarium.

The viruses can be respiratory such as, but not limited to, flu, common cold, coronaviruses including COVID-19, severe acute respiratory syndrome (SARS); gastrointestinal such as, but not limited to, norovirus and rotavirus; exanthematous such as, but not limited to, measles, rubella, shingles, smallpox; hepatic such as, but not limited to, hepatitis A, hepatitis B, hepatitis C; cutaneous such as, but not limited to, warts and herpes; hemorrhagic such as, but not limited to, Ebola, dengue fever, yellow fever; neurologic such as, but not limited to, polio, viral meningitis, viral encephalitis.

With reference to FIG. 1, a schematic depiction of an example of a light bulb 10 is illustrated. In general, the light bulb 10 includes a housing 12 with an interior space 14, a means, such as a screw-thread base (illustrated in FIGS. 2-5), to mount the light bulb 10, a plurality of white light emitting diodes (LEDs) 16 in the interior space 14 for emitting white light, and a plurality of blue LEDs 18 in the interior space for emitting ultraviolet (UV) light. The UV light emitted by the blue LEDs can have any wavelength in the UV spectrum. In one embodiment, the UV light can have a nominal wavelength of between about 320 nm to about 365 nm. This disclosed range is intended to include the end points 320 nm and 365 nm, as well as ±5-10 nm from each end point and all wavelengths between the end points. In one embodiment, the blue LEDs 18 emit UV light with a nominal wavelength of about 365 nm. In another embodiment, the blue LEDs 18 emit UV light with a nominal wavelength of about 320 nm.

In one embodiment, the light bulb 10 is devoid of phosphor through which UV light emitted by the blue LEDs 18 passes for converting the energy in the emitted UV light to visible light (i.e. the light bulb 10 can be devoid of phosphor through which the UV light emitted by the blue LEDs 18 passes to condition the emitted UV light). In another embodiment, the light bulb 10 can include suitable phosphor so that the UV light emitted by the blue LEDs 18 excites the phosphor to desirably condition the emitted UV light. In another embodiment described further below, the light bulb can include a UV light indicator that externally indicates that the blue LEDs 18 are emitting UV light where, in one embodiment, the indicator can include a phosphor that is excited by the UV light to fluoresce and thereby externally indicate that the light bulb is emitting UV light.

Returning to FIG. 1, a diffuser 20 is positioned in front of the LEDs 16. The diffuser 20 can be made of any transparent or semi-transparent material, such as glass or plastic, to diffuse the white light emitted by the LEDs 16. The diffuser 20 can be located inside the interior space 14 or the diffuser 20 can be positioned to form part of the housing 12.

With continued reference to FIG. 1, in some embodiments, a visible wavelength filter 22 is positioned relative to the blue LEDs 18, for example in front of the blue LEDs 18, to filter out visible wavelengths of the UV light emitted by the blue LEDs 18. An example of a suitable filter 22 that can be used is available from JNS Glass & Coatings of Yorkville, Ill. The filter 22 can be located inside the interior space 14 or the filter 22 can be positioned to form part of the housing 12.

A partition 24 separates white light emitted by the white LEDs 16 from UV light emitted by the blue LEDs 18. The partition 24 can be a wall or other separator that is optically opaque to prevent the emitted white light and the emitted UV light from intermixing before being emitted from the light bulb 10.

The light bulb 10 may also be configured as a smart bulb. For example, the bulb 10 can be provided with one or more controllers 30 that is configured to control (i.e. adjust) the operation of various parts of the light bulb 10. For example, the controller 30 can be electrically connected to the LEDs 16, 18 to control the operation of the LEDs 16 and/or the LEDs 18 based on a control signal received from one or more sensors 32 integrated with the light bulb 10. For example, the controller 30 can turn some or all of the LEDs 16, 18 on or off, and/or control a level of power that is applied to the LEDs 16, 18 (in which case the controller 30 can be considered a power controller). The sensor(s) 32 can include, but is not limited to, one or more of a distance sensor that senses a distance of a person and/or animal and/or inanimate structure from the light bulb 10; a motion sensor, for example a passive infrared (PIR) sensor, that senses movements of a person and/or animal in a room in which the light bulb 10 is installed; a pathogen sensor that senses pathogens (e.g. bacteria or viruses) in the room; and other types of sensors.

Figure 16:
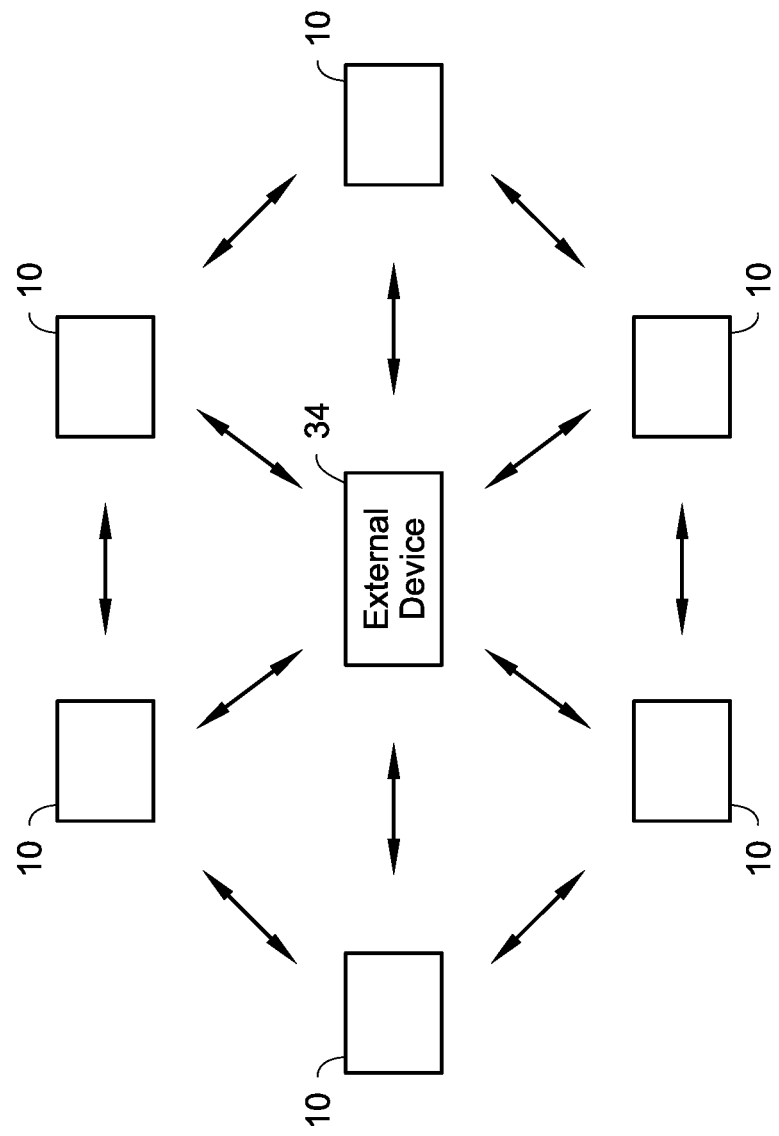
FIG. 16 is a schematic depiction of a system described herein that includes a plurality of the light bulbs described herein.

With reference to FIGS. 1 and 16, the light bulb 10 may also be in communication with one or more external devices 34 and/or with other ones of the light bulbs 10. In such instance, the light bulb 10 can include a communication transceiver 36 to permit wireless communications with other devices such as the device(s) 34 and/or other ones of the bulbs 10. The communications can include receipt of external signals from the external device 34 and/or one or more of the other bulbs 10 that can be used to control operation of the light bulb 10. The operation of the LEDs 16 and/or the operation of the LEDs 18 can be controlled based on one or more signals received from the at least one external device 34 and/or received directly or indirectly from one of the other bulbs 10. The external device 34 can include, but is not limited to, a mobile phone; a tablet computer; a laptop computer; a digital assistant; a server; a UV camera; the cloud; and a pathogen sensor.

In one embodiment, the light bulb 10 has a color rendering index (CRI) of at least 70. For example, the CRI can be at least 70 when the white LEDs 16 and the blue LEDs 18 are in simultaneous operation, or when the white LEDs 16 are in operation and the blue LEDs 18 are not in operation. In another embodiment, the light bulb 10 has a CRI of at least 80. For example, the CRI can be at least 80 when the white LEDs 16 and the blue LEDs 18 are in simultaneous operation, or when the white LEDs 16 are in operation and the blue LEDs 18 are not in operation. In still another embodiment, the light bulb 10 has a CRI of at least 90. For example, the CRI can be at least 90 when the white LEDs 16 and the blue LEDs 18 are in simultaneous operation, or when the white LEDs 16 are in operation and the blue LEDs 18 are not in operation.

FIGS. 2-5 illustrate an example implementation of the light bulb 10. In FIGS. 2-5, elements that are similar to elements in FIGS. 1 and 16 are referenced using the same reference numerals. The bulb 10 includes the housing 12 with a screw-thread base 40 attached to a base of the housing 12 for threading the light bulb 10 into a threaded socket. The screw-thread base 40 can be a conventional screw-thread base construction having threads for screwing the bulb 10 into a conventional threaded socket. For example, the screw-thread base 40 can be E26, E27, E11, E12, E14, E17, E39 or E40. In some embodiments, the light bulb 10 need not include a screw-thread base and other forms of light bulb mounting and electrical connection can be used.

Figure 3:
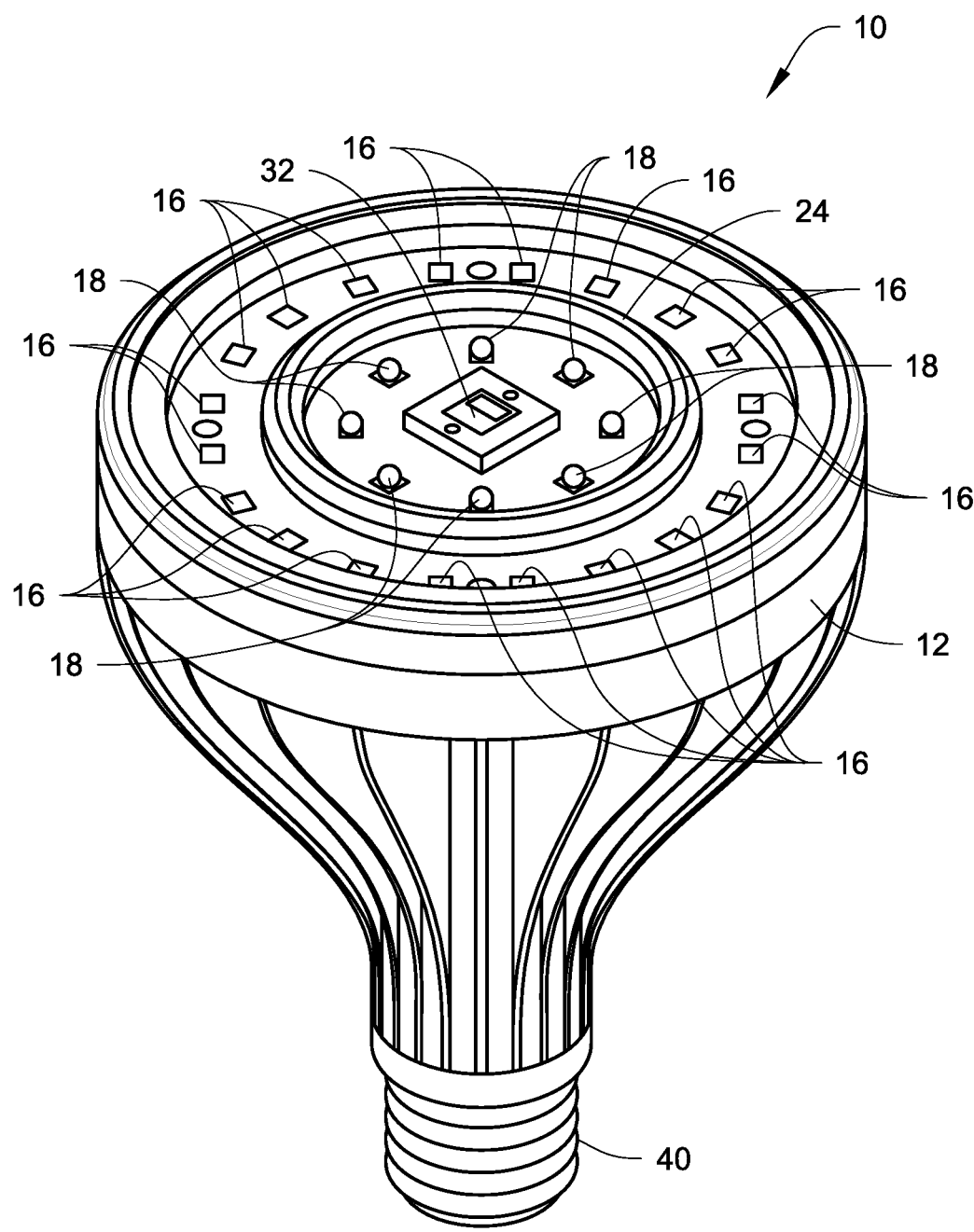
FIG. 3 is a perspective view similar to FIG. 2 but with the diffuser and the visible wavelength filter removed.
Figure 4:
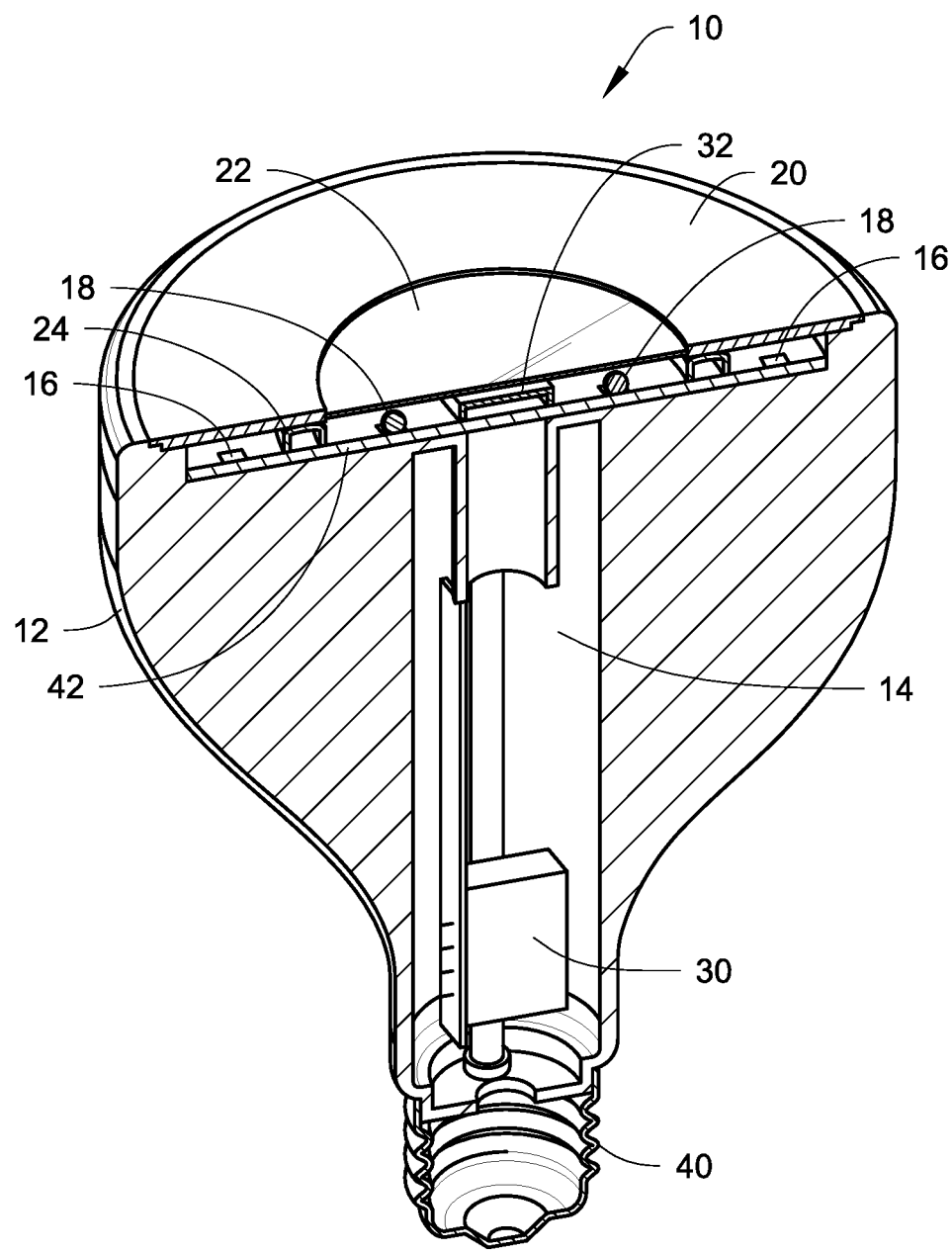
FIG. 4 is a cross-sectional perspective view through the center of the light bulb of FIG. 2.
Figure 5:
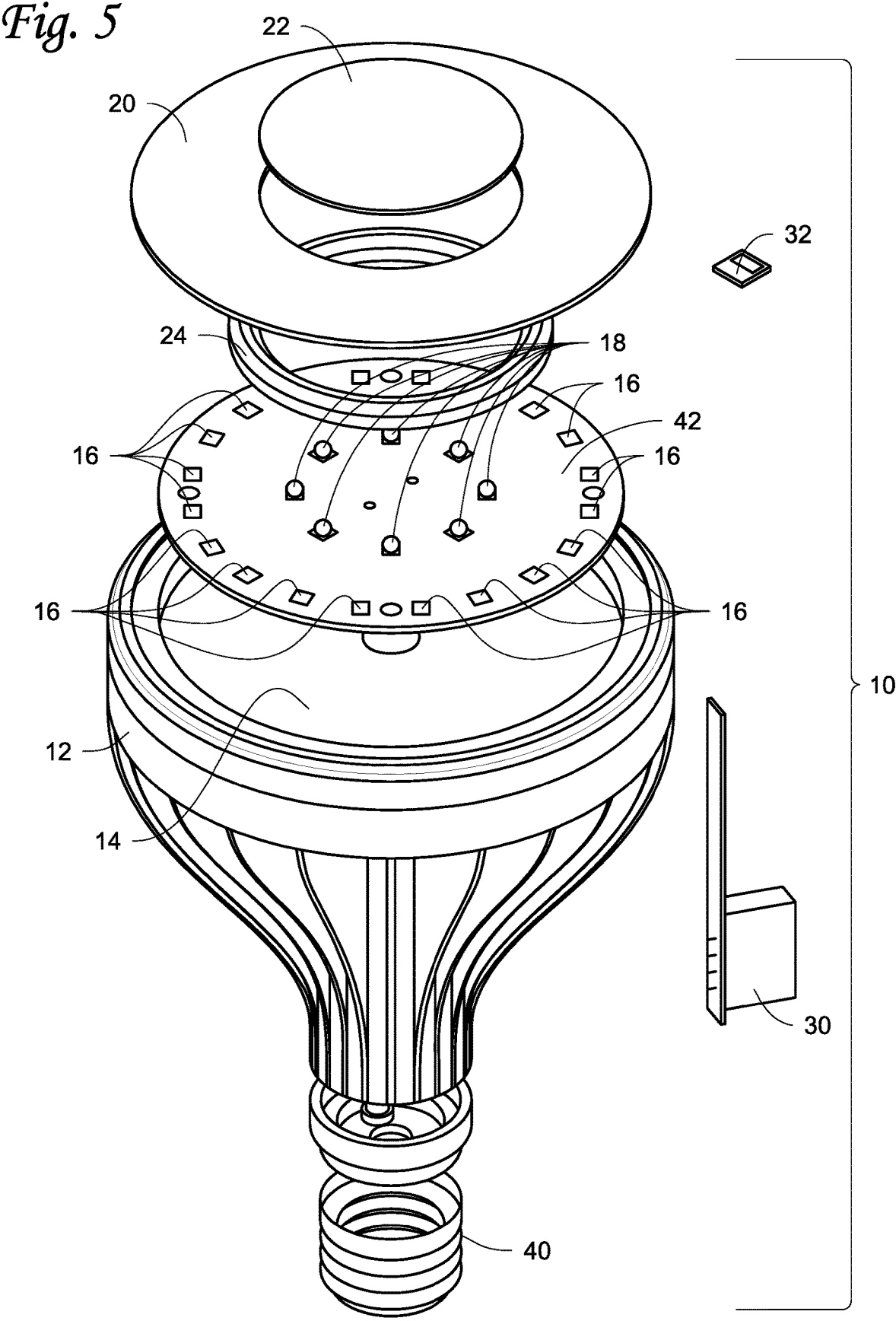
FIG. 5 is an exploded perspective view of the primary components of the light bulb in FIG. 2.

In the example illustrated in FIGS. 3-5, the LEDs 16 are illustrated as being arranged in a circular array surrounding the LEDs 18. The LEDs 18 are also illustrated as being arranged in a circular array surrounded by the LEDs 16. However, other arrangements of the LEDs 16, 18 are possible. As best seen in FIGS. 4 and 5, the LEDs 16, 18 are disposed on a support substrate 42 such as a circuit board. In one embodiment, there is no phosphor in the light bulb 10 through which the UV light emitted by the blue LEDs 18 to condition the UV light emitted by the blue LEDs 18.

Referring to FIGS. 4 and 5, the partition 24 is disposed between the arrays of LEDs 16, 18 to prevent white light from the LEDs 16 from mixing with the UV light from the LEDs 18 until each of the white light and the UV light exits the bulb 10. As best seen in FIG. 4, the partition 24 extends from the top surface of the circuit board 42 to the interior surface of the diffuser 20 to provide complete separation of the white light and the UV light.

With continued reference to FIGS. 4 and 5, the sensor 32 is depicted as being disposed on the support substrate 42 proximate the center of the bulb 10. However, other locations of the sensor 32 are possible. The sensor 32 can be located at any location that permits the sensor 32 to performs its sensing function(s).

As also depicted in FIGS. 4 and 5, the controller 30 can be located within the interior space 14 of the bulb 10. The controller 30 can be located at any location in or on the bulb 10 that permits the controller 30 to perform its control function(s). In the depicted example, the controller 30 is shown as being disposed in a neck of the bulb 10 within the interior space 14 that extends into the neck.

In an embodiment, the UV light emitted by the light bulb 10 can have a wavelength and output power that is safe for humans and pets during normal use of the bulb 10 and the UV light inactivates pathogens over relatively prolonged exposure periods, for example at least about 10 minutes, at least about 20 minutes, at least about 30 minutes, at least about 1 hour, at least about 8 hours, or at least about 24 hours. In addition, the UV light emitted by the light bulb may be at a wavelength and power level that are safe for continuous human or animal exposure at a distance of at least 1 meter from the light bulb 10 for at least 2 hours, and the UV light has a wavelength and a power whereby pathogens located at least 1 meter from the light bulb that are continually exposed to the UV light for at least 2 hours are inactivated. In another embodiment, the UV light emitted by the light bulb may be safe for continuous human exposure at a distance of at least 1 meter for at least 8 hours, or for at least 24 hours.

In an embodiment, the light bulb 10 can be controlled so that the controller 30 adjusts the power level provided to the LEDs 18 based on one or more signals from the sensor 32. For example, if the sensor 32 does not sense a human or animal in the room, the power provided to the LEDs 18 may be increased so that the power level of the UV light output from the LEDs 18 is increased to a higher level that may be harmful to a human or animal if one were present in the room. In an embodiment, the wavelength of the UV light output from the light bulb 10 may be altered if the sensor 32 does not sense a human or animal in the room, for example by deactivating one set of blue LEDs 18 having a first nominal wavelength and activating a second set of blue LEDs 18 that have a second nominal wavelength that may be more effective at deactivating pathogens in a shorter time but that may be harmful to a human or animal if one were present in the room. If the sensor 32 detects a human or animal entering the room, the power level of the LEDs 18 can be adjusted and/or the output wavelength of the UV light emitted by the light bulb 10 can be adjusted back to a level that is safe for humans and animals.

In addition, the bulb 10 can be controlled to emit both the white light and the UV light simultaneously. In another embodiment, the bulb 10 can be controlled to emit just the white light, and the UV light is not emitted, for example by deactivating the blue LEDs 18. In another embodiment, the bulb 10 can be controlled to emit just the UV light and the white light is not emitted, for example by deactivating the LEDs 16.

FIGS. 6-9 illustrate another embodiment of a light bulb 50. In FIGS. 6-9, elements that are similar to elements in FIGS. 1-5 are referenced using the same reference numerals. The bulb 50 includes the housing 12 with the screw-thread base 40 or other means attached to an end of the housing 12 for threading the light bulb 50 into a threaded socket. The screw-thread base 40 can be a conventional screw-thread base construction having threads for screwing the bulb 50 into a conventional threaded socket. For example, the screw-thread base 40 can be E26, E27, E11, E12, E14, E17, E39 or E40. In some embodiments, the light bulb 50 need not include a screw-thread base and other forms of light bulb mounting and electrical connection can be used.

The light bulb 50 includes the plurality of white light emitting diodes (LEDs) 16 in the interior space 14 for emitting white light, and the plurality of blue LEDs 18 in the interior space for emitting ultraviolet (UV) light. The UV light emitted by the blue LEDs 18 can have any wavelength in the UV spectrum. In one embodiment, the UV light can have a nominal wavelength of between about 320 nm to about 365 nm. This disclosed range is intended to include the end points 320 nm and 365 nm, as well as ±5-10 nm from each end point and all wavelengths between the end points. In one embodiment, the blue LEDs 18 emit UV light with a nominal wavelength of about 365 nm. In another embodiment, the blue LEDs 18 emit UV light with a nominal wavelength of about 320 nm. In one embodiment, the light bulb 50 can have a color rendering index (CRI) of at least 70. In another embodiment, the light bulb 50 can have a CRI of at least 80. In still another embodiment, the light bulb 50 can have a CRI of at least 90. The light bulb 50 can also have a color temperature of around 3200 k.

Figure 6:
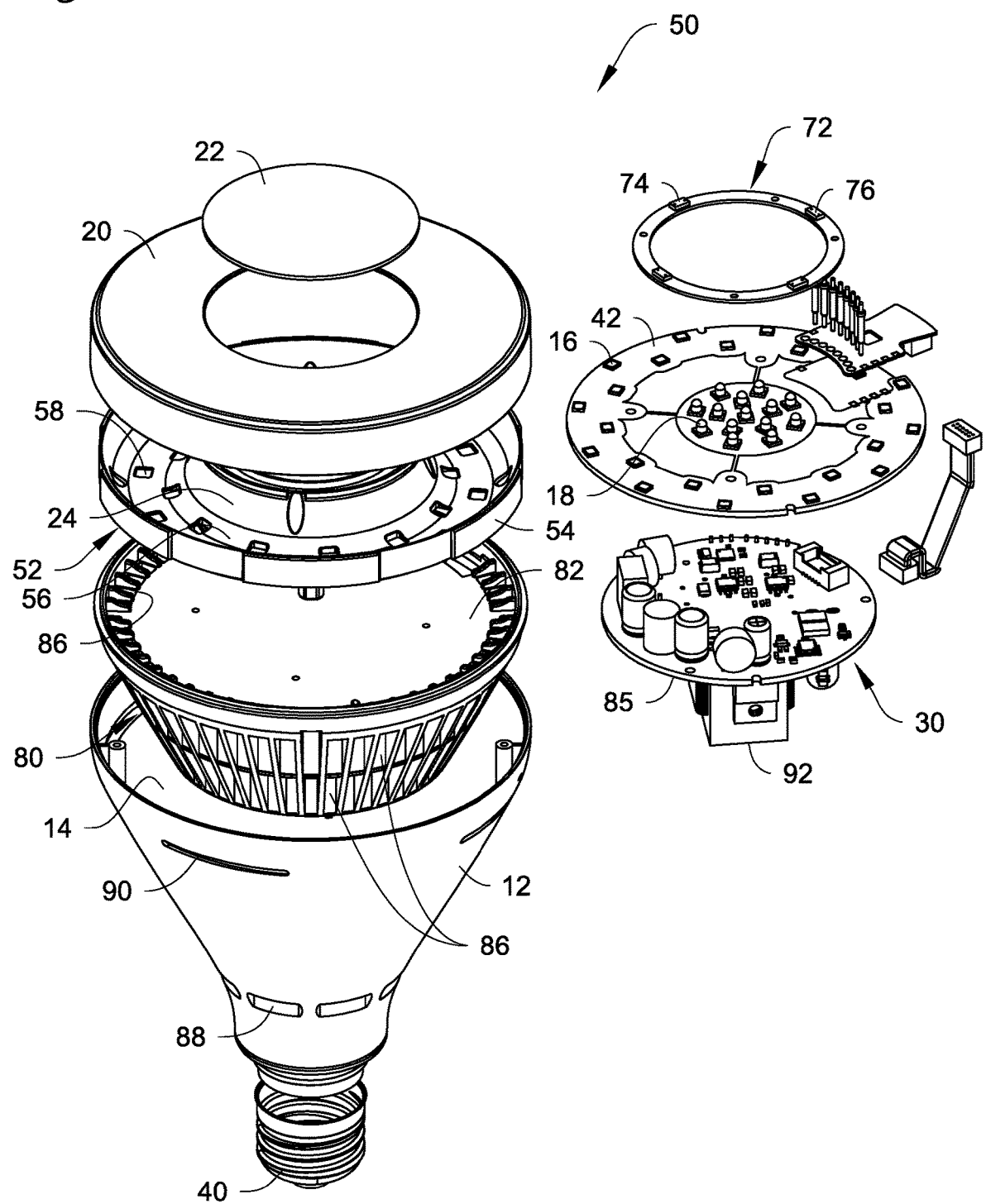
FIG. 6 is an exploded perspective view of another embodiment of a light bulb described herein.

In the example illustrated in FIG. 6, the LEDs 16 are illustrated as being arranged in an array, for example a circular array, surrounding the LEDs 18. However, other arrangements of the LEDs 16, 18 are possible. As best seen in FIG. 6, the LEDs 16, 18 are disposed on the support substrate 42 such as a circuit board.

Figure 8:
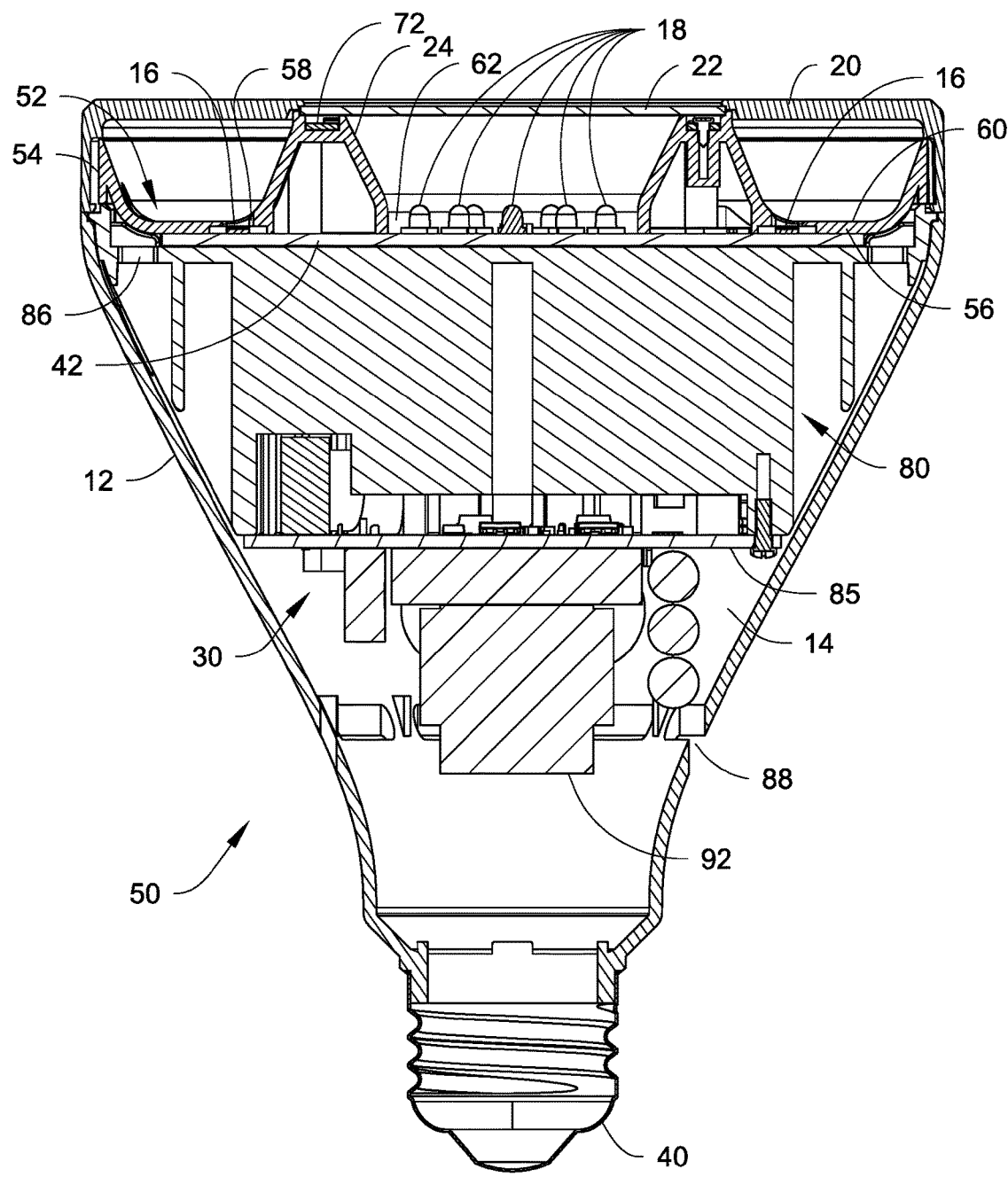
FIG. 8 is a cross-sectional side view taken along line 8-8 of FIG. 7.

Referring to FIGS. 6 and 8, a partition assembly 52 that forms the partition 24 is disposed in the bulb 50 to prevent white light from the LEDs 16 from mixing with the UV light from the LEDs 18 until each of the white light and the UV light exits the bulb 50. As best seen in FIG. 8, the partition 24 extends from the top surface of the circuit board 42 to the interior surface of the filter 22 to provide complete separation of the white light and the UV light. The partition assembly 52 can be formed from a material that can transfer heat within the light bulb 50. For example, the partition assembly 52 can be formed from a metal such as aluminum or copper, or a thermally conductive plastic. The partition assembly 52 includes a perimeter portion 54 that is spaced from the partition 24 by a base portion 56 that in use rests on and is engaged with the circuit board 42. The base portion 56 includes a plurality of openings 58 formed therein that receive the LEDs 16 to allow the LEDs 16 to extend through the base portion 56.

The partition assembly 52 further includes a central opening 62 surrounded by the partition 24. The central opening 62 faces the visible wavelength filter 22 and receives the LEDs 18 to allow the UV light emitted by the LEDs 18 to reach the filter 22.

The diffuser 20 is positioned in front of the LEDs 16 and the diffuser facing surfaces 60. The diffuser 20 can be made of any transparent or semi-transparent material, such as glass or plastic, to diffuse the white light emitted by the LEDs 16. In addition, the visible wavelength filter 22 is positioned relative to the blue LEDs 18, for example in front of the blue LEDs 18, to filter out visible wavelengths of the UV light emitted by the blue LEDs 18. An example of a suitable filter 22 that can be used is available from JNS Glass & Coatings of Yorkville, Ill. In the illustrated example, the filter 22 is a circular disc that is opaque, for example that is solid black in color or other color that is suitable for filtering out the visible wavelengths of the UV light emitted by the LEDs 18 while permitting non-visible wavelengths of UV light to pass. In one embodiment, the filter 22 can be supported on the end of the partition 24, sandwiched between the diffuser 20 and the end of the partition 24.

Figure 7:
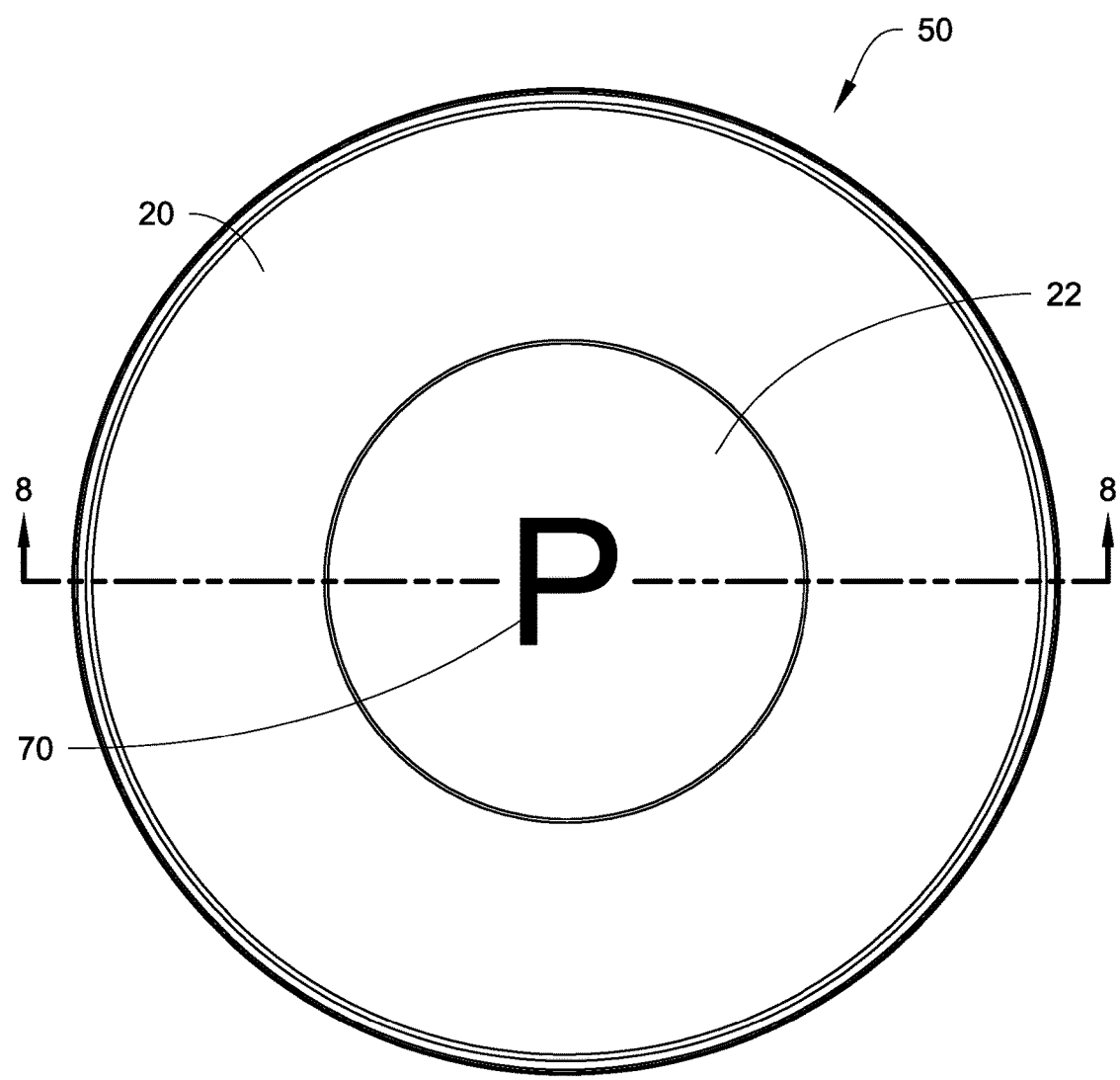
FIG. 7 is an end view of the light bulb in FIG. 6.

The bulb 50 can include a UV light indicator that is visible externally of the light bulb 50 to externally indicate to a user that the bulb 50 is emitting UV light. The UV light indicator can be implemented in any manner that is suitable to externally indicate to a user that UV light is being emitted. For example, with reference to FIG. 7, a UV light indicator 70 is depicted as being incorporated into the filter 22. In one example, the UV light indicator 70 can be formed by phosphor that is incorporated into the filter 22. When the phosphor of the indicator 70 is exposed to UV light emitted by the LEDs 18, the phosphor is excited by the UV light to fluoresce so as to be visible to the naked eye and thereby externally indicate that the light bulb 50 is emitting UV light. When UV light is not being emitted and the phosphor is not excited, the indicator 70 is preferably not visible to the naked eye. FIG. 7 depicts the phosphor of the light indicator 70 in a fluoresced condition. The phosphor can be incorporated into the filter 22 in any manner and at any location that permits the excited phosphor to be visible to the naked eye externally of the bulb 50. The phosphor of the indicator 70 can be arranged into any shape or design including, but not limited to, a logo, a name, a letter (as depicted in FIG. 7), a number, a ring, a circle, a square, a rectangle, a triangle, a star, a symbol, and many others. In another embodiment, the indicator 70 can be a portion of the filter 22 that is modified, for example by etching, in a manner to permit a small amount of visible light emitted by the LEDs 18 to pass through the filter 22. For example, the UV light indicator 70 depicted in FIG. 7 can indicate visible light emitted by the LEDs 18 passing through the filter 22. In another embodiment, the UV light indicator 70 can be an indicator light, such as an LED (separate from the LEDs 16, 18), that is mounted on the bulb 50 so as to be visible to the naked eye and which is controlled by the controller 30 to be illuminated when UV light is being emitted.

In one embodiment, the light bulb 50 is devoid of phosphor, separate from any phosphor that may be used in the indicator 70 whose purpose is not to condition the UV light emitted by the LEDs 18, through which the UV light emitted by the LEDs 18 passes to condition the emitted UV light. In another embodiment, the light bulb 50 can include suitable phosphor located on the bulb 50 so that the UV light emitted by the LEDs 18 excites the phosphor to desirably condition the emitted UV light.

The light bulb 50 may also be configured as a smart bulb. For example, referring to FIG. 6, the bulb 50 can be provided with the one or more controllers 30 that is configured to control (i.e. adjust) the operation of various parts of the light bulb 50. For example, the controller 30 can be electrically connected to the LEDs 16, 18 to control the operation of the LEDs 16 and/or the LEDs 18 based on a control signal received from one or more sensors on a sensor assembly 72 integrated with the light bulb 50. For example, the controller 30 can turn some or all of the LEDs 16, 18 on or off, and/or control a level of power that is applied to the LEDs 16, 18 (in which case the controller 30 can be considered a power controller). The controller 30 can be located within the interior space of the bulb 50. However, the controller 30 can be located at any location in or on the bulb 50 that permits the controller 30 to perform its control function(s).

The sensor assembly 72 can include, but is not limited to, at least one sensor such as one of the sensors described above for the bulb 10. In one embodiment, the sensor assembly 72 can include a distance sensor 74 that senses a distance of a person and/or animal and/or inanimate structure from the light bulb 50; a motion sensor 76, for example a passive infrared (PIR) sensor, that senses movements of a person and/or animal in a room in which the light bulb 50 is installed; a pathogen sensor that senses pathogens (e.g. bacteria or viruses) in the room; and other types of sensors. With reference to FIGS. 6 and 8, the sensor assembly 72 can be positioned proximate the center of the bulb 50. However, other locations of the sensor assembly 72 and the sensors thereon are possible. The sensors can be located at any location that permits the sensors to performs their sensing functions. In this example, the sensor assembly 72 is depicted as a ring that is disposed underneath and adjacent to the filter 22 and sandwiched between the filter 22 and the partition 24, with the ring including circumferentially spaced sensing elements forming the sensors. One of the sensors on the sensor assembly 72 may be a PIR sensor for sensing motion.

With reference to FIG. 16, the light bulb 50 in FIGS. 6-9 may also be in communication with one or more external devices 34 and/or with other ones of the light bulbs 50. In such instance, the light bulb 50 can include a communication transceiver, similar to the transceiver 36 in FIG. 1, to permit wireless communications with other devices such as the device(s) 34 and/or other ones of the bulbs 50. The communications can include receipt of external signals from the external device 34 and/or one or more of the other bulbs 50 that can be used to control operation of the light bulb 50. The operation of the LEDs 16 and/or the operation of the LEDs 18 can be controlled based on one or more signals received from the at least one external device 34 and/or received directly or indirectly from one of the other bulbs 50. The external device 34 can include, but is not limited to, a mobile phone; a tablet computer; a laptop computer; a digital assistant; a server; a UV camera; the cloud; and a pathogen sensor.

In an embodiment, the UV light emitted by the light bulb 50 can have a wavelength and output power that is safe for humans and pets during normal use of the bulb 50 and the UV light inactivates pathogens over relatively prolonged exposure periods, for example at least about 10 minutes, at least about 20 minutes, at least about 30 minutes, at least about 1 hour, at least about 8 hours, or at least about 24 hours. In addition, the UV light emitted by the light bulb 50 may be at a level that is safe for continuous human or animal exposure at a distance of at least 1 meter for at least 2 hours, and the UV light has a wavelength and a power whereby pathogens located at least 1 meter from the light bulb 50 that are continually exposed to the UV light for at least 2 hours are inactivated. In another embodiment, the UV light emitted by the light bulb 50 may be safe for continuous human exposure at a distance of at least 1 meter for at least 8 hours, or for at least 24 hours.

In an embodiment, a light bulb generally similar in construction to the light bulb 50 was tested to determine the efficacy of virus inactivation. The tested light bulb emitted UV light at a nominal wavelength of 365 nm and at an irradiance level of about $0.5$ watts/m$^2$±$0.05$ watts/m$^2$. The light bulb was found to inactivate the COVID-19 virus by about 94.7% at 5 hours of exposure to the emitted UV light, by about 99.2% at 6 hours of exposure to the emitted UV light, and by about 99.9% at 8 hours of exposure to the emitted UV light. In another embodiment, another light bulb was tested to determine the efficacy of virus inactivation. The tested light bulb emitted UV light at a nominal wavelength of 365 nm and at an irradiance level of about 2.5 watts/m$^2$±0.05 watts/m$^2$. The light bulb was found to inactivate the COVID-19 virus by 100% at 4 hours of exposure to the emitted UV light.

In an embodiment, the light bulb 50 can be controlled so that the controller thereof adjusts the power level provided to the LEDs 18 based on one or more signals from the sensor(s) of the sensor assembly 72. For example, if the sensor assembly 72 does not sense a human or animal in the room, the power provided to the LEDs 18 may be increased so that the power level of the UV light output from the LEDs 18 is increased to a higher level that may be harmful to a human or animal if one were present in the room. In some embodiments, the wavelength of the UV light output from the light bulb 50 may be altered if the sensor assembly 72 does not sense a human or animal in the room, for example by deactivating one set of the LEDs 18 having a first nominal wavelength and activating a second set of the LEDs 18 that have a second nominal wavelength that may be more effective at deactivating pathogens in a shorter time but that may be harmful to a human or animal if one were present in the room. If the sensor assembly 72 detects a human or animal entering the room, the power level of the LEDs 18 can be adjusted and/or the output wavelength of the UV light emitted by the light bulb 50 can be adjusted back to a level that is safe for humans and animals.

In addition, the bulb 50 can be controlled to emit both the white light and the UV light simultaneously. In another embodiment, the bulb 50 can be controlled to emit just the white light, and the UV light is not emitted, for example by deactivating the LEDs 18. In another embodiment, the bulb 50 can be controlled to emit just the UV light and the white light is not emitted, for example by deactivating the LEDs 16.

In one embodiment, the light bulb 50 can include a distance sensor and a motion sensor. The controller 30 is operatively connected to the distance sensor, the motion sensor, the LEDs 16 and to the LEDs 18 in a manner so that the light bulb 50 can be automatically controlled by the controller 30 to operate in a plurality of different modes. For example, the light bulb 50 can be controlled to automatically operate in, and automatically switch between, any one of the following operational modes:

16, 18 to dim (i.e. change the power level) in one or more of the modes. In another embodiment, there can be one set of the blue LEDs 18 that emit UV light at one wavelength and one or more additional sets of blue LEDs 18 that emit UV light at another wavelength, and the light bulb 50 can switch between the different sets of blue LEDs 18.

Figure 21:
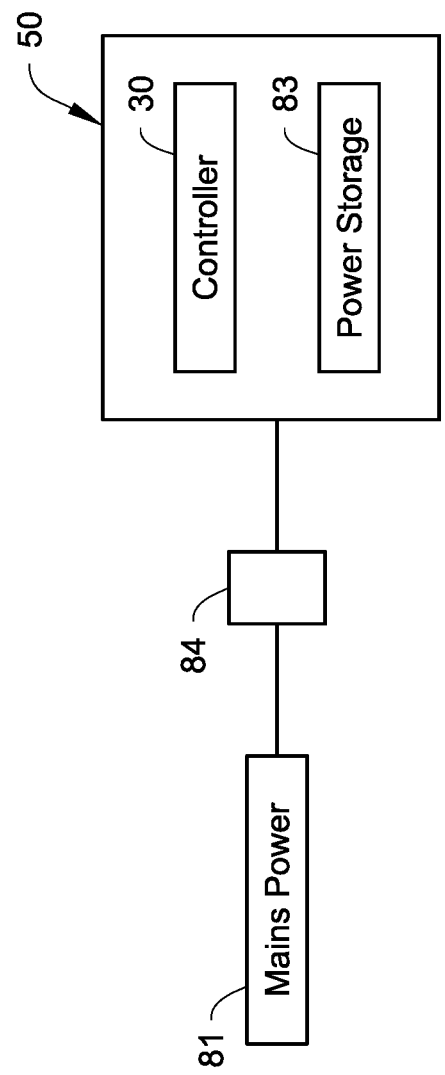
FIG. 21 is a schematic depiction of a light bulb described herein controlled by a switch and powered by mains power.

With reference to FIG. 21, the motion sensor and the distance sensor can be controlled to operate continuously anytime the light bulb 50 is switched-on and receiving mains power 81. In one embodiment, the light bulb 50 can include a power storage device 83, such as a battery or a capacitor, that includes a charge sufficient to operate the sensor(s) and the controller 30 to change the operational mode of the light bulb 50 based on feedback from the sensor(s). In another embodiment, the operational mode of the light bulb 50 can be manually changed, for example using the external device 34 in FIG. 16, or through use of a switch 84 (seen in FIG. 21), such as a wall switch, based on a predetermined on/off switch rate of the switch 84. For example, switching the switch 84 on/off in quick succession over a period of time can cause a change in the operational mode of the bulb 50. For example, switching the switch 84 on/off five times in five seconds can change the operational mode of the bulb 50. An example of controlling an operational state of a light bulb based on detected switch rate is described in U.S. Pat. No. 9,210,779, the entire contents of which are incorporated herein by reference.

Figure 9:
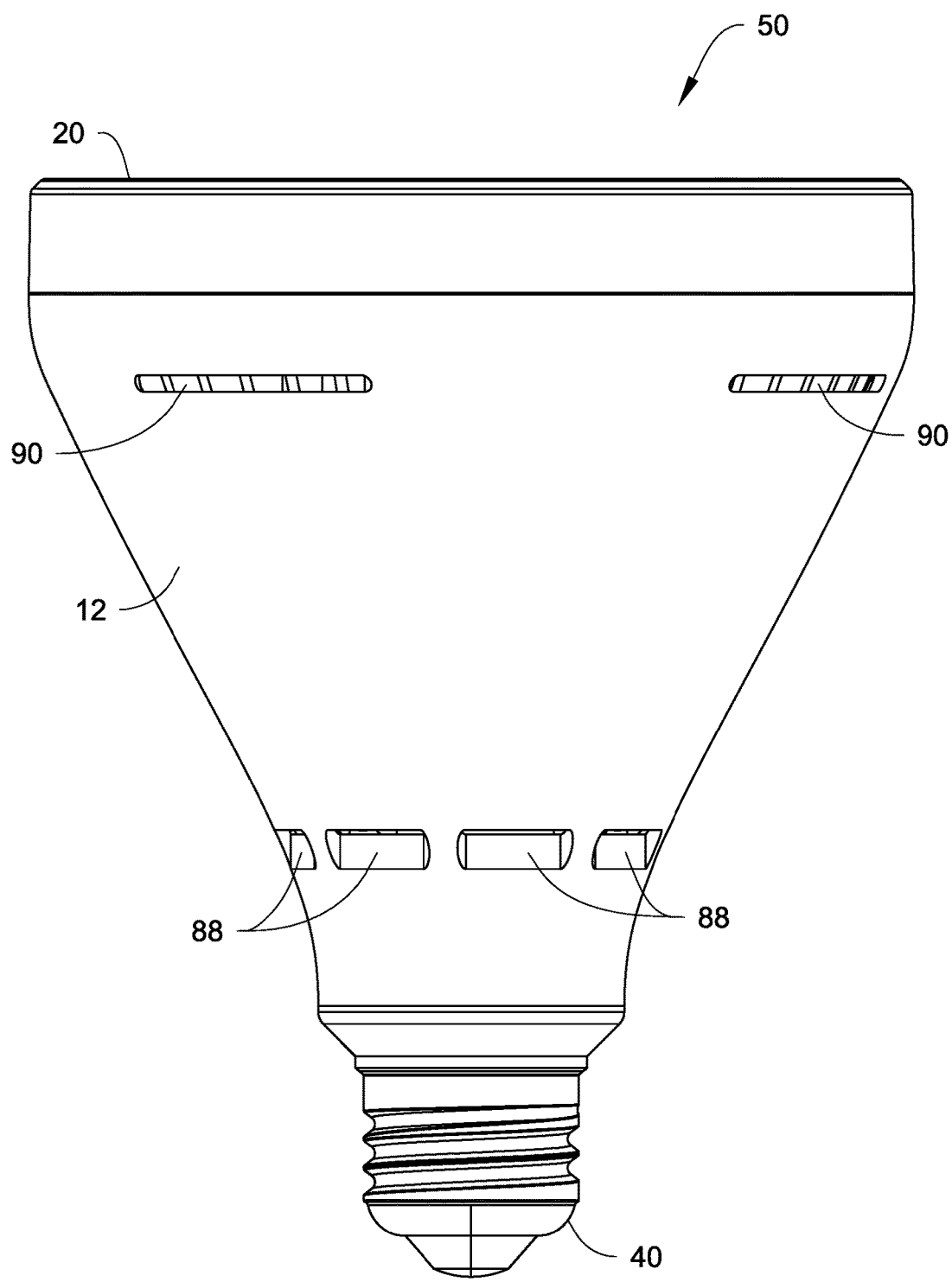
FIG. 9 is a side view of the light bulb of FIGS. 6-8.

With reference to FIGS. 6 and 8-9, the light bulb 50 can also be provided with cooling features to help dissipate heat generated by the LEDs 16, 18 and other electronics of the light bulb 50. For example, the light bulb 50 can include a cooling insert 80 that helps to passively dissipate heat. The cooling insert 80 is made of any material(s) suitable for conducting heat including, but not limited to, aluminum. The insert 80 is configured as a structure that fills a substantial amount of the interior space 14. The cooling insert 80 includes a surface 82 at one end that is engaged with the circuit board 42 as best seen in FIG. 8 to draw heat away heat generated by the LEDs 16, 18. The opposite end of the insert 80 is recessed and receives electronics associated with the controller 30 mounted on a circuit board 85 which can be fastened to the insert 80.

With continued reference to FIGS. 6 and 8-9, the insert 80 further includes a number of air flow passages 86 therethrough. The air flow passages 86 allow air flow through the

TABLE 1

|  | No Motion Sensed By The Motion Sensor | | Motion Sensed By The Motion Sensor | | Person Within Threshold Range To Light Bulb | |
| --- | --- | --- | --- | --- | --- | --- |
|  | LEDs 18 | LEDs 16 | LEDs 18 | LEDs 16 | LEDs 18 | LEDs 16 |
| Mode 1 | ON | ON | ON | ON | OFF | ON |
| Mode 2 | ON | ON | OFF | ON | OFF | ON |
| Mode 3 | ON | OFF | ON | ON | OFF | ON |
| Mode 4 | ON | OFF | OFF | ON | OFF | ON |

The threshold range in Table 1 above can vary based on the nominal wavelength of the UV light emitted by the LEDs 18. In one embodiment, assuming the LEDs 18 emit UV light with a nominal wavelength of 365 nm, the threshold range in Table 1 above can be around 1 meter whereby the LEDs 18 are controlled to shut-off if the distance sensor determines that a person or animal is within 1 meter of the light bulb 50.

In Table 1 above, instead of binary on/off control of the LEDs 16, 18, the light bulb 50 may also control the LEDs insert 80 that removes heat from the insert 80. In the illustrated example, the air flow passages 86 are formed around the perimeter edge at the surface 82 and then extend through the insert 80 to openings at the side of the insert 80. A plurality of cooling air openings 88, 90 are formed in housing 12 to permit airflow through the light bulb 50 including through the insert 80. In the illustrated example, the openings 88 are formed in the bulb 50, for example in the housing 12, adjacent to the screw-thread base 40 and the openings 90 are formed in the bulb 50, for example in the housing 12, adjacent to the diffuser end of the bulb 50. In one embodiment, the openings 88 can be cooling air inlet openings through which cooling air enters the bulb 50, and the openings 90 can be cooling air outlet openings through which the cooling air exits the bulb 50. In another embodiment, the openings 90 can be cooling air inlet openings through which cooling air enters the bulb 50, and the openings 88 can be cooling air outlet openings through which the cooling air exits the bulb 50. In one embodiment, the flow of the cooling air into, through, and from the bulb 50 can be due to convection. In another embodiment, the bulb 50 can include a fan 92 to supplement the convection air flow or to cause the cooling air to flow in a direction opposite what would be convection air flow direction. The fan 92 can be located at any location in the bulb 50 that is suitable for causing a flow of air through the interior space 14 of the bulb 50 from one set of the openings 88, 90 to the other set of openings 88, 90. For example, as best seen in FIGS. 6 and 8, the fan 92 can be mounted on the circuit board 85. The fan 92 may be a reversible fan to allow the direction of the air flow to be changed depending upon the rotation direction of the fan 92. The light bulb 50 can include an orientation sensor incorporated therein that detects the orientation of the bulb 50 which is used to control the rotation direction of the fan 92. To facilitate air flow, the perimeter edge of the circuit board 85 can be spaced from the wall of the housing 12 to allow air to flow past the circuit board 85. In addition, the circuit board 85 can include holes or other air passageways therein to allow the air to flow past the circuit board 85. In one embodiment, the total area of the openings 88 and the total area of the openings 90 can be in a ratio of 1 to 1. However, the total area of the openings 88 can be greater than the total area of the openings 90, or the total area of the openings 90 can be greater than the total area of the openings 88.

Any of the features of the bulb 50 can be used individually in a light bulb. In addition, any one or more of the features of the bulb 10 in FIGS. 2-5 can be used in combination with any one or more features of the bulb 50 in FIGS. 6-9.

With reference now to FIGS. 10-15, another embodiment of a light bulb 100 will now be described. The light bulb 100 may be configured as a smart light bulb that is configured to wirelessly communicate with one or more external devices including, but not limited to, a mobile device such as a mobile phone or a tablet, or a pathogen sensor. Any of the features of the bulb 100 can be used individually in a light bulb. In addition, any one or more of the features of the bulb 100 can be used in combination with any one or more features of the bulb 10 in FIGS. 2-5 and/or with any one or more features of the bulb 50 in FIGS. 6-9.

In an embodiment, the light bulb in FIGS. 10-15 can include at least one light emitting diode (LED), such as a blue LED, and a phosphor is associated with the light bulb cover and/or the at least one LED to generate the white light. In some embodiments, the light bulb can include multiple LEDs each of which can be coated with a different phosphor. In other embodiments, the light bulb can include at least one LED, such as a blue LED, that generates the UV light, and the white light is generated from one or more additional non-UV LEDs with or without phosphor. In still another embodiment, the white light can be generated from a portion of the UV light emitted by one or more blue LEDs combining with light emitted by one or more additional LEDs, such as one or more LEDs that emit yellow light that emit light in a wavelength of between about 550 nm to about 650 nm, whereby no phosphor needs to be used in the light bulb. Different combinations of LED colors can be used to achieve the desired perceived color output, including colors other than white, and brightness. In one embodiment, the different LEDs can be constantly energized when power is supplied to the light bulb. In another embodiment, the different LEDs can be controllably energized when power is supplied to the light bulb, individually and/or in different combinations thereof, to achieve different lighting and UV light emission.

The light bulb 100 produces UV light and a desired perceived colored light output. The brightness and desired color output can be produced using at least one LED, such as a blue LED, and a phosphor, and the color output can be perceived as white light. The brightness and desired color output can be produced using at least one LED, such as a blue LED, together with one or more additional LEDs. The one or more additional LEDs may be coated with a phosphor, for example to generate white light. In still another embodiment, the desired color output, such as white light, can be generated from a portion of the UV light emitted by one or more blue LEDs combining with light emitted by one or more additional LEDs, such as one or more LEDs that emit yellow light that emit light in a wavelength of between about 550 nm to about 650 nm, whereby no phosphor needs to be used in the light bulb. Different combinations of LED colors can be used to achieve the desired perceived color output, including colors other than white, and brightness.

Figure 10:
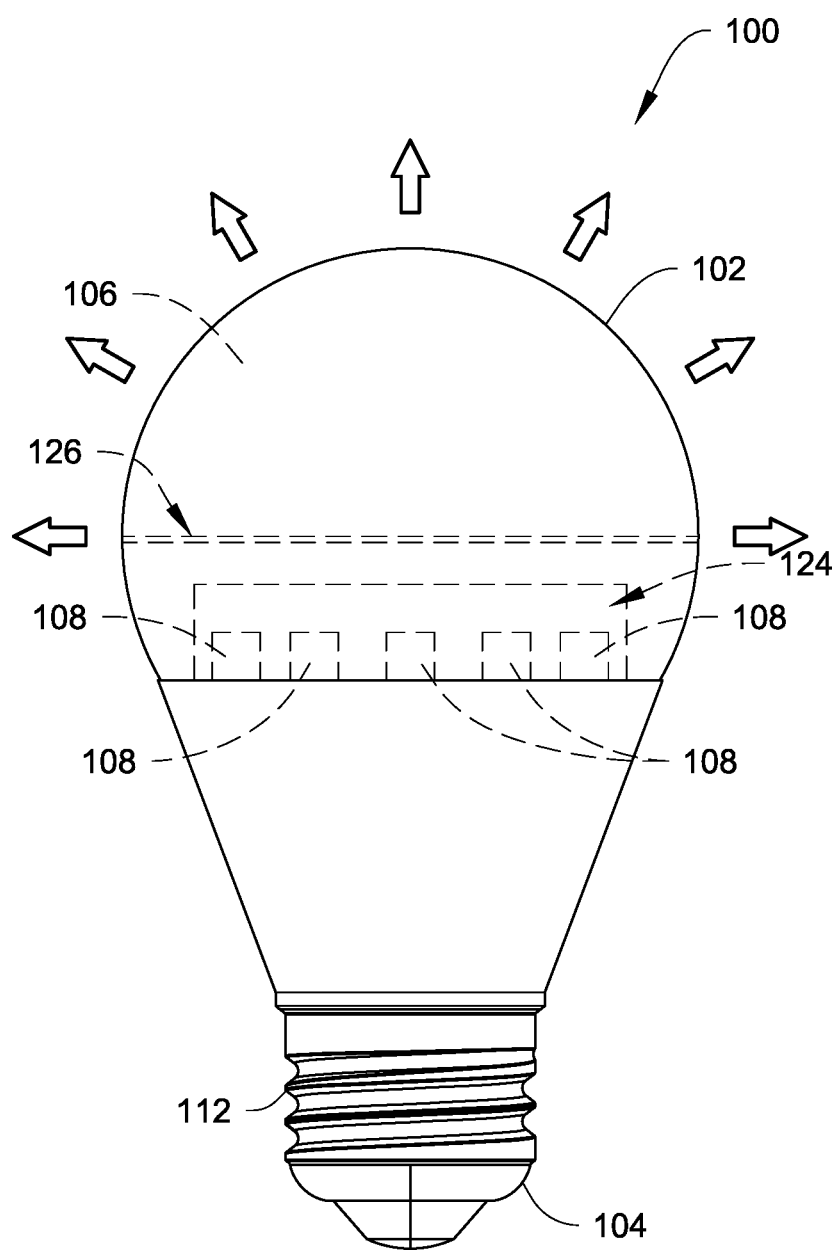
FIG. 10 illustrates another embodiment of a light bulb described herein.

FIG. 10 illustrates an example of the light bulb 100 that is constructed and functions as described herein. The light bulb 100 includes a cover 102 which may also be referred to as a globe, a bulb, or a diffuser. A screw-thread base 104 is attached to the cover 102 for threading the light bulb 100 into a threaded socket (not shown) similar to a conventional screw-thread light bulb. The cover 102 and the screw-thread base 104 define an enclosed space 106, and at least one LED 108 is disposed in the enclosed space 106. In this example, the LED 108 can be a blue LED that emits UV light, and the light bulb 100 can include a phosphor that generates white light when energized by UV light incident thereon. The light bulb 100 emits white light and also emits UV light that is safe for humans and has a wavelength and output power that is sufficient to inactivate pathogens that are exposed to the UV light for a prolonged period of time.

The cover 102 can be made of the same materials used to form covers in conventional light bulbs including, but not limited to, glass and plastic. The cover 102 can be clear or transparent, or translucent.

The screw-thread base 104 can be a conventional screw-thread base construction having threads 112 for screwing the bulb 100 into a conventional threaded socket. For example, the screw-thread base 14 can be E26, E27, E11, E12, E14, E17, E39 or E40. In some embodiments, the light bulbs 100 need not include a screw-thread base and other forms of light bulb mounting and electrical connection can be used.

The embodiment in FIG. 10 illustrates five of the LEDs 108, each of which can be a blue LED configured to emit UV light when activated. However, a smaller or larger number of the blue LEDs 108 can be used. The LEDs 108 can be intended to emit the same wavelength or each LED 108 can be intended to emit a different wavelength of UV light. In one embodiment, each one of the LEDs 108 emits UV light having a wavelength and output power that is safe for human and pet exposure to the UV light. In an embodiment, each one of the LEDs 108 emits UV light having a wavelength that is equal to or greater than about 320 nm and less than or equal to about 420 nm. In another embodiment, each one of the LEDs 108 emits UV light having a wavelength that is within a range of about 320 nm to about 395 nm. In still another embodiment, at least one of the LEDs 108 emits UV light having a wavelength that is equal to about 365 nm or equal to about 395 nm. In one embodiment, the maximum output power of the LED 108 can be between about 50 Watts to about 180 Watts at 1 meter from the light bulb 100. In another embodiment, the maximum output power of the LED 108 can be at least about 50 Watts at about 5 feet from the light bulb 100.

Figure 11:
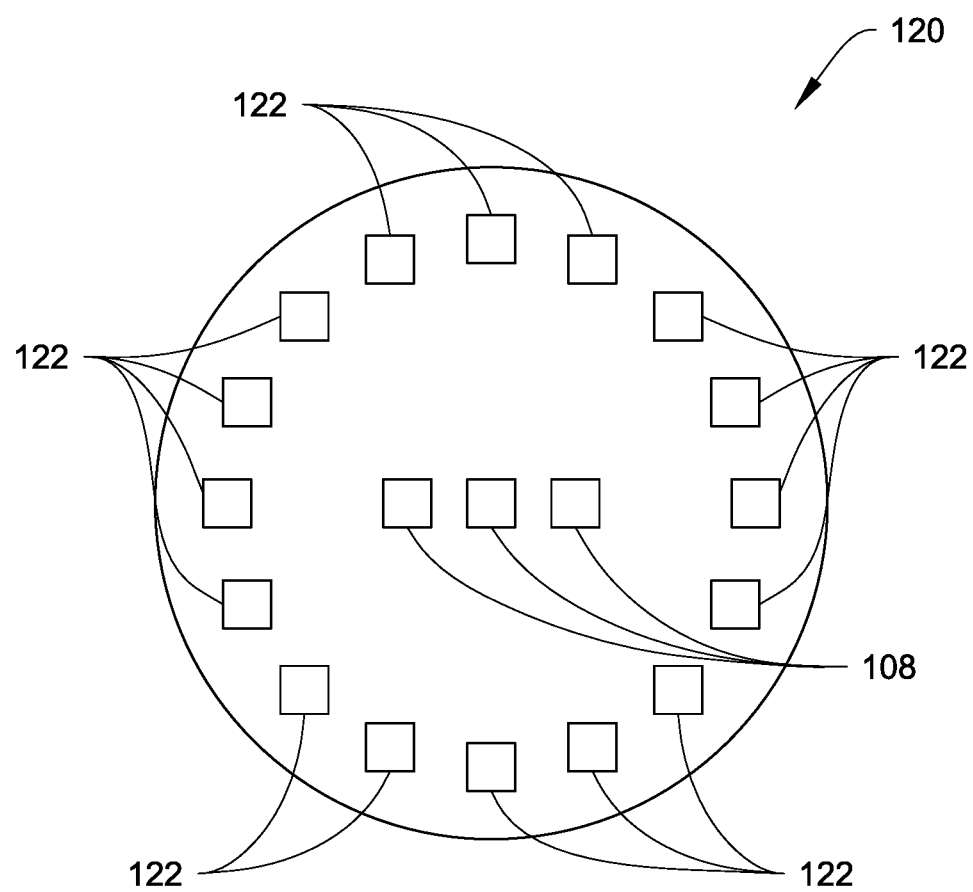
FIG. 11 is a top view of an array of LEDs that can be used in the light bulb of FIG. 10.

FIG. 11 illustrates a top view of an array 120 of LEDs that can be used in the light bulb 100 in FIG. 10. The array 120 includes a plurality of the LEDs 108 that emit the UV light component, and one or more additional, non-UV LEDs 122. The non-UV LEDs 122 can be configured to generate the white light emitted by the light bulb. In the array 120, the UV light emitted by the LEDs 108 does not energize a phosphor. In one embodiment, the LEDs 122 can be referred to as white light LEDs that include an LED and a suitable phosphor that are configured to output the white light component of the light bulb. In the illustrated example, the LEDs 122 can be arrayed in a circular arrangement surrounding the LEDs 108. In another embodiment, no phosphor is used in the light bulb 100. Instead, the one or more non-UV LEDs 122 can be one or more yellow LEDs that emit light in a wavelength range of between about 550 nm to about 650 nm which combines with a portion of the UV light emitted by the LED(s) 108 to generate the white light. In other embodiments, the non-UV LEDs 122 can emit colors other than or in addition to yellow, such as red and/or green, and the non-UV LEDs 122 can be separately controlled from one another to control the perceived color output of the light bulb 100.

Inactivation of pathogens and danger to humans from UV light both are dependent on wavelength, intensity, and duration of exposure. Intensity also varies with distance from the source of the UV light, such as the LED(s) 108. The intensity of the LED(s) 108 used in the light bulb 100 can be selected based on their nominal wavelength. The selection of intensity by nominal wavelength can be a range having boundaries including an upper boundary based on safety for continuous human exposure. In an embodiment, the ranges can be based on the intensity an LED would provide to surfaces at typical or approximated distances from the light bulb 100 to those surfaces. In an embodiment, the ranges for the intensity of LEDs 108 are based on the intensity of light from the LEDs 108 at a surface that is a distance of one meter from the light bulb 100. In an embodiment, the upper boundary is based on the maximum permissible exposure to UV light according to guidelines provided by the International Commission on Non-Ionizing Radiation Protection (ICNIRP). The ICNIRP guidelines suggest that UV exposure should not exceed 30 J/m$^2$ over an 8-hour period. In an embodiment, a lower boundary for the intensity of the LEDs 108 is approximately one quarter of the value of the upper boundary. In an embodiment, the lower boundary for the intensity of the LEDs 108 can be based on an amount of light of that wavelength required to be effective to inactivate one or more selected pathogens to a desired level over a typical or approximated duration for use of the light bulb 100, such as, for example, ten minutes, one hour, four hours, or eight hours, or 24 hours.

In an embodiment, the upper boundary of the range for the intensity of LEDs 108 can be based on an effective irradiance value for a wavelength or range of wavelengths provided by the LEDs 108. The effective irradiance value can be scaled based on the nominal wavelength of light provided by LEDs 108. The upper boundary can then be based on an intensity that provides a maximum effective irradiance of less than 30 J/m$^2$ over the course of 8 hours of continuous exposure. An LED, such as the LED 108, having an intensity at or below the upper boundary cannot exceed the threshold for safe human exposure, and thus is safe for continuous exposure. In an embodiment, the intensity of the UV light emitted by LEDs 108 to the ambient environment in which the light bulb 100 is used can be within the ranges for wattage for a given nominal wavelength of the LED 108 as provided below, from about 270 nm wavelength to about 400 nm:

| Ranges for Intensity of LED by Wavelength | | |
|---|---|---|
| Nominal Wavelength (nm) | Lower Boundary (W) | Upper Boundary (W) |
| 220 or less | 0.0133 | 0.0532 |
| 221-230 | 0.0088 | 0.0350 |
| 231-240 | 0.0058 | 0.0230 |
| 241-250 | 0.0038 | 0.0152 |
| 251-260 | 0.0025 | 0.0100 |
| 261-279 | 0.0016 | 0.0066 |
| 280-289 | 0.0019 | 0.0074 |
| 290-299 | 0.0026 | 0.0103 |
| 300-309 | 0.0055 | 0.0219 |
| 310-319 | 0.1103 | 0.4411 |
| 320-329 | 1.3013 | 5.2051 |
| 330-339 | 3.6599 | 14.6396 |
| 340-349 | 5.6868 | 22.7471 |
| 350-359 | 8.3150 | 33.2601 |
| 360-369 | 12.1060 | 48.4239 |
| 370-379 | 17.6201 | 70.4804 |
| 380-389 | 25.6454 | 102.5816 |
| 390-394 | 37.3258 | 149.3033 |
| 395-400 | 45 | 180 |

As described above, the light bulb 100 in FIG. 10 can include a phosphor which is energized by the UV light emitted by the LED 108 to generate the white light. The phosphor is positioned in the light bulb 100 so that the UV light emitted by the LED(s) 108 impacts the phosphor and excites the phosphor electrons to generate white light for illumination. The phosphor can be positioned anywhere in the light bulb 100 as long as the UV light from the LED(s) 108 impacts and energizes the phosphor to generate the white light. For example, in the embodiment illustrated in FIG. 10, the LED(s) 108 can be embedded in and surrounded by phosphor 124. In an alternative embodiment, a layer of phosphor 126 can be disposed in the bulb 10 so that the UV light emitted by the LED(s) 18 impacts the phosphor layer 126. In other embodiments, the phosphor can be a layer or coating on an interior surface of the cover 102, or the phosphor can be blended in with the material forming the cover 102.

The phosphor can be any phosphor or combination of phosphors that result in the features of the light bulbs described herein. The phosphor can be white phosphor (FIG. 13), green phosphor (FIG. 14), red phosphor (FIG. 15) and combinations thereof.

In the example of the LED 108 being a blue LED that emits UV light at a nominal wavelength of about 395 nm, the phosphor can be configured such that the total output light from the bulb 100 can be approximately 70% UV light at about 395 nm and about 30% white light resulting from energizing the phosphor. However, LEDs that emit different wavelengths and different types, compositions, and mixtures of phosphors can be used to achieve different ratios of UV light to white light output from the light bulb 100.

Figure 12:
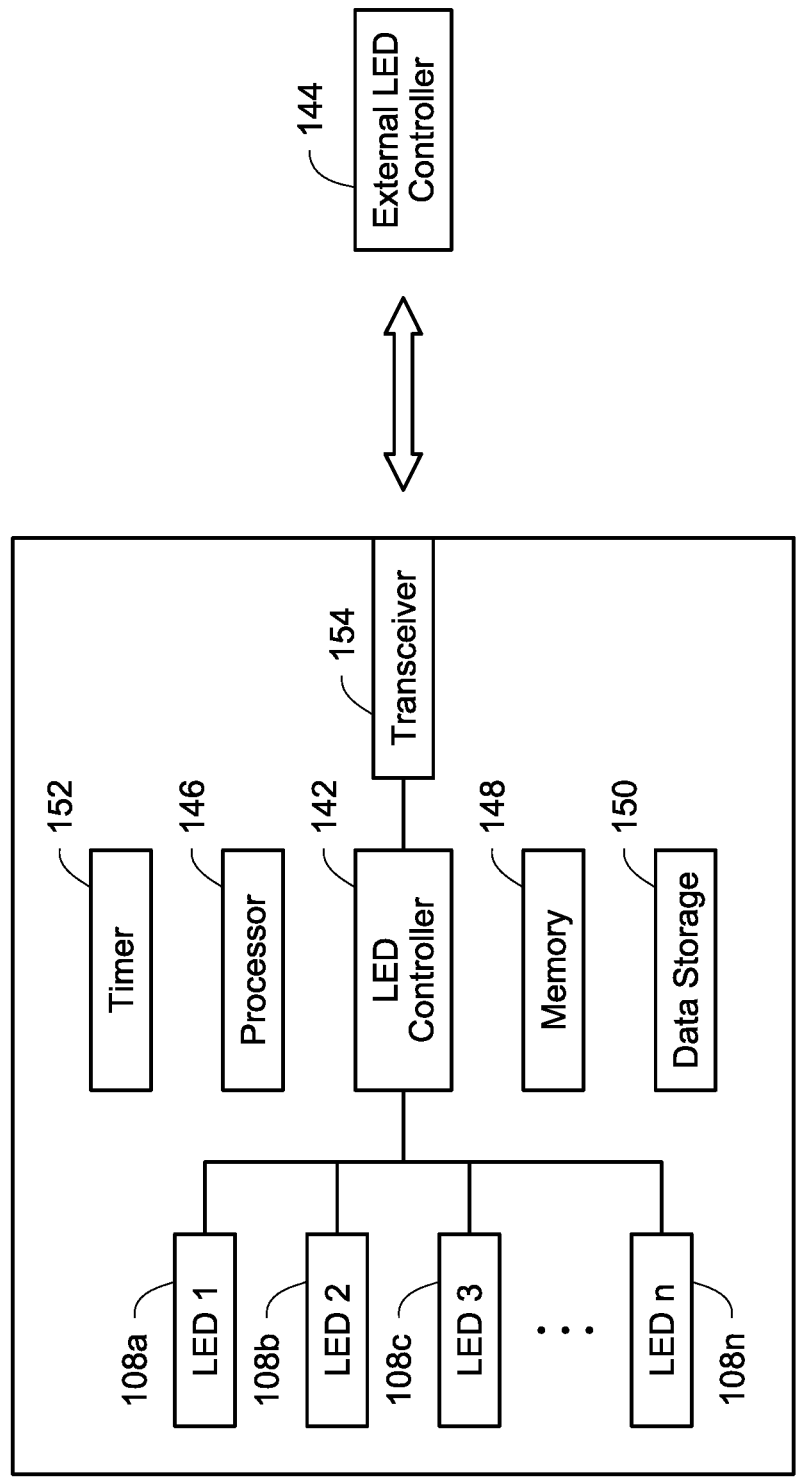
FIG. 12 illustrates an example of controlling the light bulb depicted in FIG. 11.
Figure 13:
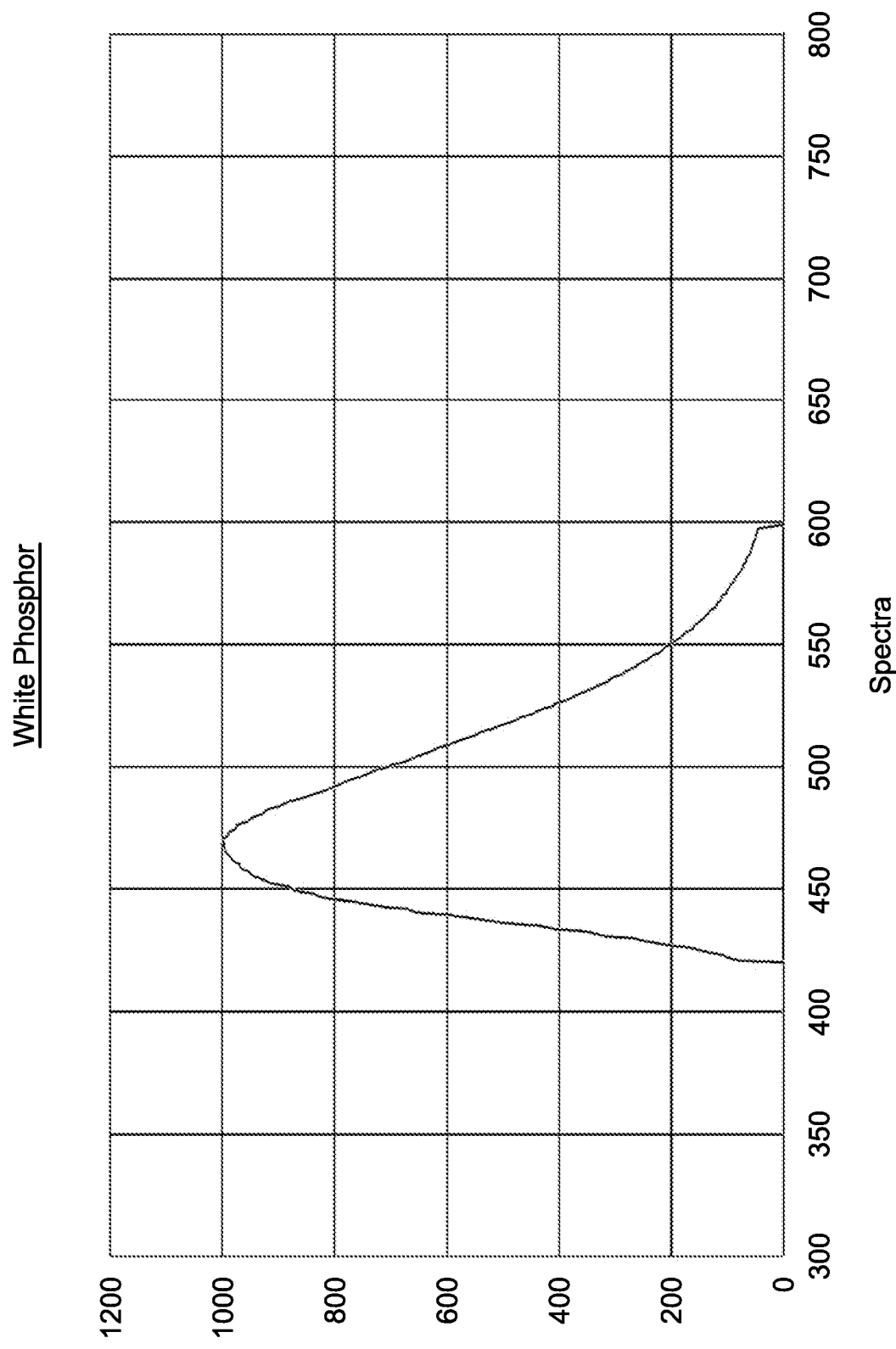
FIG. 13 illustrates a spectral curve of an example of white phosphor.
Figure 14:
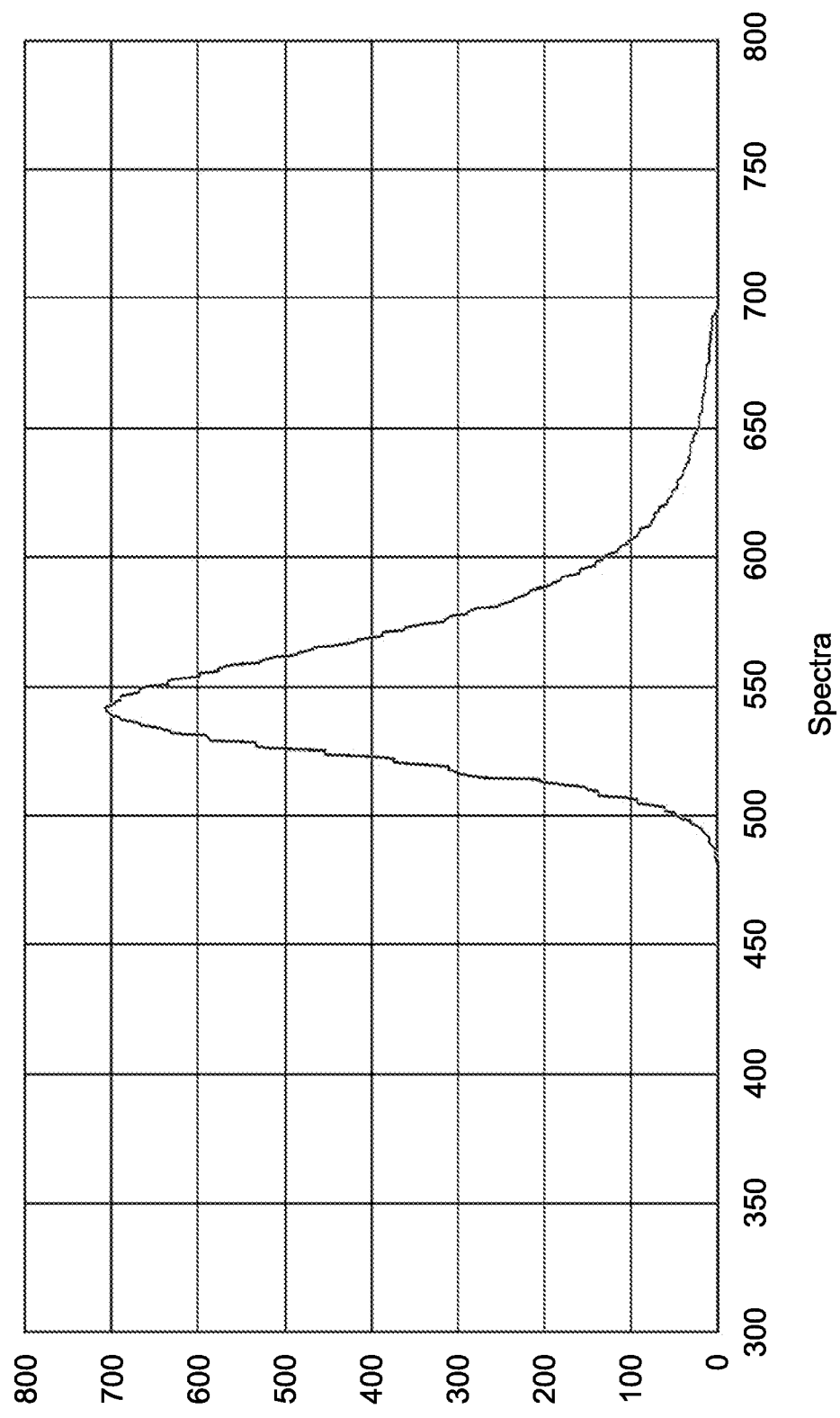
FIG. 14 illustrates a spectral curve of an example of nitride green phosphor.
Figure 15:
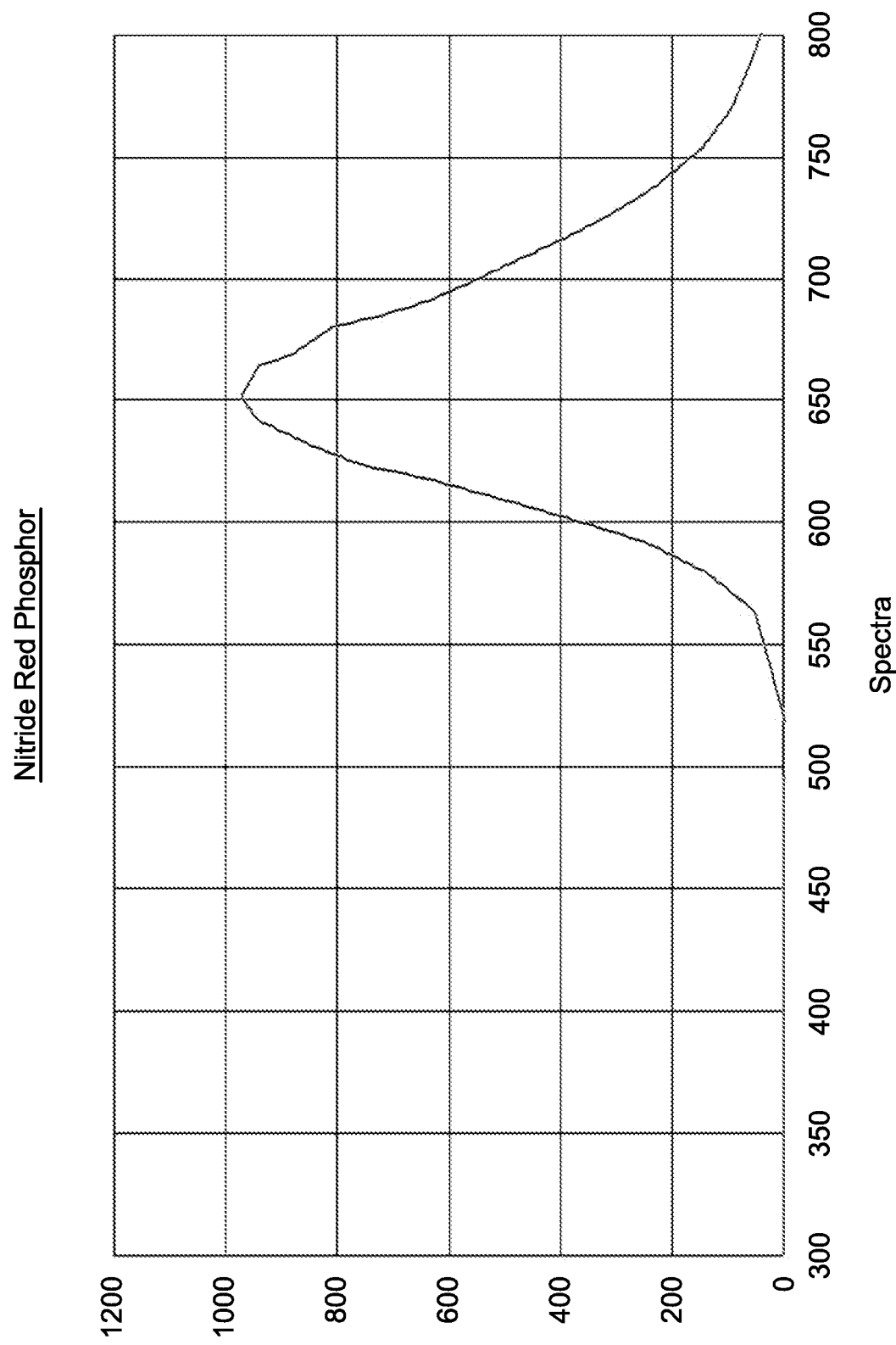
FIG. 15 illustrates a spectral curve of an example of nitride red phosphor.

FIG. 12 schematically illustrates an example of a light bulb that can include a number of features in common with FIG. 10. In FIG. 12, features that are similar or identical to features in FIG. 10 are referenced using the same reference numerals. In this example, the light bulb includes a plurality of separately controllable LEDs 108a, 108b, ... 108n.

The LEDs 108a, 108b, ... 108n can be different LEDs that emit different wavelengths of UV light. For example, the LEDs 108a, 108b, ... 108n can each be a blue LED, with one blue LED emitting blue UV light having a first wavelength, another blue LED emitting blue UV light having a second wavelength, etc. In another embodiment, the LEDs 108a, 108b, ... 108n can be identical, for example blue LEDs that emit the same wavelength of blue UV light, but are coated with different phosphors to achieve different white light output. In still another embodiment, the LEDs 108a, 108b, ... 108n can have different wavelength outputs and have different phosphor coatings.

By selectively controlling which of the LEDs 108a, 108b, ... 108n is activated, the white light illumination and the UV light output and thus the pathogen inactivation capabilities, of the light bulb can be controlled. The LEDs 108a, 108b, ... 108n can be activated individually or simultaneously. For example, the LED 108a can be configured for pathogen inactivation over a first exposure time period, the LED 108b can be configured for pathogen inactivation over a second exposure time period that can be greater or lesser than the first exposure time period, etc. In another embodiment, the LED 108a can be configured to emit a wavelength that is suitable to inactivate a first type of pathogen, while the LED 108b can be configured to emit a wavelength that is suitable to inactivate a second type of pathogen.

Control of the light bulb in FIG. 12 can occur via a controller 142 internal to the light bulb or via an external controller 144. The controller 142 is connected to each one of the LEDs 108a, 108b, ... 108n. In the case of a control scheme internal to the light bulb, the light bulb can include a data processor 146 for executing one or more computer control instructions or programs stored in memory 148. The light bulb can also include data storage 150 for storing data pertaining to the operation of the light bulb, for example from external sensors, sensors incorporated into the light bulb, the length of time that each LED 108a, 108b, ... 108n is activated, and many others. The light bulb may also include a timer 152 which can be used as part of, for example, a control scheme where two or more of the LEDs 108a, 108b, ... 108n are controlled so as to be activated for periods of time. For external communications, the light bulb may also include a transceiver 154 which can receive external communications, for example from the external controller 144, or transmit communications externally, for example transmit a health report relating to the usage of the LEDs and their estimated remaining life. In an embodiment, the controller 142 can be configured to control the light output of the light bulb, including the UV output and/or the perceived color output, based on a wall switch that controls the light fixture to which the light bulb. The control can be achieved based on the number of times the wall switch is quickly switched on and off. For example, switching the wall switch on and off 3 times in quick succession can result in a first UV light output and/or a first color output from the light bulb, while switching the wall switch on and off 4 times in quick succession can result in a second UV light output and/or a second color output from the light bulb.

The light bulbs in FIGS. 10-12 herein emit both white light for illumination and UV light that is safe for humans and pets and that has a wavelength and output power that is sufficient to inactivate pathogens that are exposed to the ultraviolet light for relatively prolonged periods of time. For example, the light bulbs can emit UV light at a wavelength that is equal to or greater than about nominal 320 nm and less than or equal to about nominal 420 nm. In another embodiment, the light bulbs emit UV light having a wavelength that is within a range of about nominal 320 nm to about nominal 405 nm. In still another embodiment, the light bulbs emit UV light having a wavelength that is equal to about nominal 395 nm. The light bulbs can also have a white light output that ranges between, for example, about 300 lumens to about 4000 lumens. The light bulbs can also have a color temperature that ranges between, for example, about 2500 K to about 6500 K.

The exposure time period for inactivating pathogens using the light bulbs in FIGS. 10-12 is measured in multiple minutes. For example, the exposure time period can be, for every 24 hours, a minimum of about 10 minutes, or a minimum of about 20 minutes, or a minimum of about 30 minutes, or a minimum of about 45 minutes, or a minimum of about 60 minutes, or a minimum of about 2 hours, or a minimum of about 4 hours, or a minimum of about 8 hours, or a minimum of about 24 hours, or the like.

Figure 17:
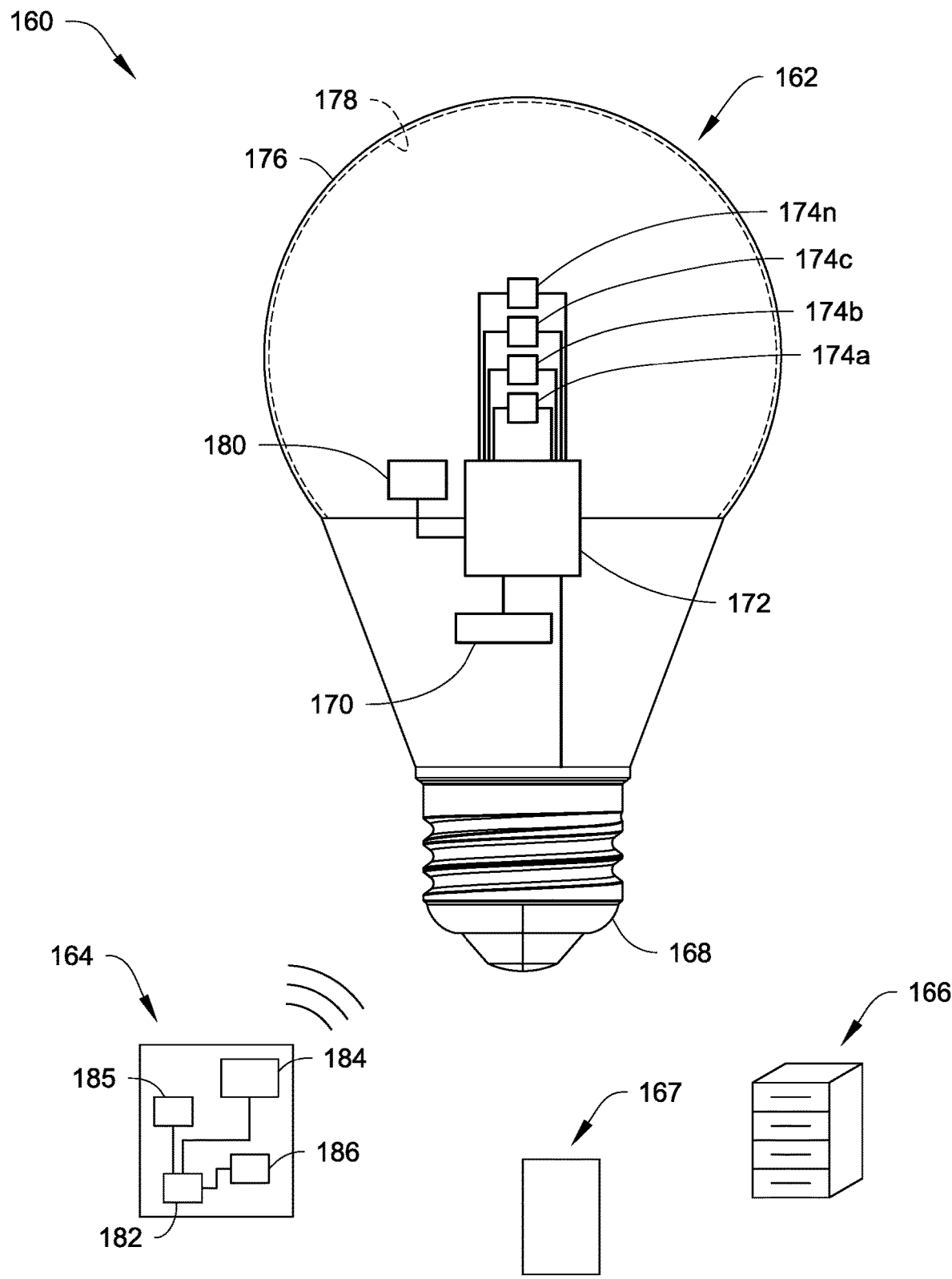
FIG. 17 shows a smart lighting system according to an embodiment.

FIG. 17 shows a smart lighting system 160 according to an embodiment. The smart lighting system 160 includes a smart light bulb 162 and remote device 164. In an embodiment, smart lighting system 160 further includes a server 166. The smart light bulb 162 includes a screw-thread base 168, a wireless communication antenna 170, a controller 172, a first light emitting diode (LED) 174a, a diffuser 176, and a phosphor 178. The smart light bulb 162 can optionally further include additional LEDs 174b-n. Any one or more of the features of the bulb 162 can be used in combination with any one or more features of the bulb 100 and/or with any one or more features of the bulb 10 in FIGS. 2-5 and/or with any one or more features of the bulb 50 in FIGS. 6-9.

The screw-thread base 168 is at an end of the smart light bulb 162. The screw-thread base 168 includes an electrical connection that allows electrical power to be received at the screw-thread base 168 and provided to the controller 172, which can then allocate that electrical power to the first LED 174a and, optionally, additional LEDs such as second LED 174b. The screw-thread base 168 can be sized and shaped to fit in any suitable threaded connection provided on a light fixture, such as any of the standard candelabra, intermediate, medium, or mogul fixtures. Examples of such standards include E11 and E12 for candelabras, E14 and E17 for intermediate sized fixtures, E26 and E27 for medium sized fixtures, and E39 or E40 for mogul fixtures. In an embodiment, the screw-thread base 168 is sized and shaped to fit in an E26 and/or an E27 sized fixture.

The wireless communication antenna 170 is a wireless communication antenna configured to receive a control signal and/or transmit signals. The wireless communication antenna 170 can be an antenna suitable for use with any suitable wireless communications protocol for providing the control signal, including but not limited to Bluetooth, Zig-Bee, Wi-Fi, any 802.11 protocols, near-field communications, or any other suitable wireless communication standard or method.

The controller 172 is a controller configured to process a control signal received by the wireless communication antenna 170, and to operate the LEDs of the smart light bulb 162 including at least the first LED 174a according to the control signal. The controller 172 processes the control signal to determine the operations dictated by the control signal. Non-limiting examples of operations directed by the control signal include: turning the light on or off, varying one or more parameters of the light supplied by the smart light bulb 162 such as intensity or color, turning the light on or off at a predetermined time, or operating the light for a predetermined amount of time. The controller is configured to control the flow of power from the electrical connection at screw-thread base 168 to the LEDs to carry out the operations of the light directed by the control signal. In an embodiment including multiple LEDs such as the second LED 174*b* in addition to the first LED 174*a*, the control of flow of power can include allocation of relative amounts of power to each of the different LEDs, for example to adjust the intensity of particular wavelengths in the light that is provided by the smart light bulb 162.

The first LED 174*a* is a light emitting diode. The first LED 174*a* can be an LED selected to provide light such that the smart light bulb 162 can provide both visible light and also ultraviolet light to a space when the first LED 174*a* is combined with phosphor 178. The first LED 174*a* can be, for example, a near ultraviolet LED. The first LED 174*a* can provide light having a wavelength of between 360 nm and 405 nm. In an embodiment, the first LED 174*a* provides light having a wavelength of between 380 nm and 405 nm. In an embodiment, the first LED 174*a* provides light having a wavelength of between 395 nm and 405 nm. The first LED 174*a* is connected to the controller 172 and/or the electrical supply from the screw-thread base 168 such that the controller 172 can control the supply of power to the first LED 174*a*.

Optionally, additional LEDs 174*b-n* can be included beyond the first LED 174*a*. In an embodiment, the additional LEDs 174*b-n* can each provide light having a wavelength different than the first LED 174*a* and any other additional LEDs 174*b-n*. In an embodiment, the smart light bulb 162 can include at least one UV LED, a red LED, and a green LED. Each of the additional LEDs can be connected to the controller 172 and/or the electrical supply from the screw-thread base 168 such that the controller 172 can control the supply of power to that additional LED 174*b-n*. In an embodiment, one of the additional LEDs can provide UV light at a wavelength different from that provided by the first LED 174*a*. In an embodiment, the wavelength of UV light provided by the additional LED 174*b-n* is a wavelength selected for its ability to make one or more pathogens exhibit fluorescence. In an embodiment, the wavelength of UV light provided by the additional LED 174*b-n* is in a range from 240 nm to 350 nm. In an embodiment, the smart light bulb 162 includes three additional LEDs 174*b-n* in addition to the first LED 174*a*, with the additional LEDs 174*b-n* respectively providing light having wavelengths of approximately 240 nm, 450 nm, and 650 nm. In an embodiment, the additional LEDs 174*b-n* included in the smart light bulb 162 produce visible white light. In an embodiment, at least one additional LED 174*b* can produce yellow light that, when combined with the UV light output by first LED 174*a*, results in light perceived as white visible light.

The diffuser 176 scatters the light output by the LEDs of the smart light bulb 162. The diffuser 176 can surround all of the LEDs of the smart light bulb 162. The diffuser 176 can be made of any suitable material for scattering the light, such as glass, plastics such as acrylics or polystyrene, or the like. The diffuser 176 can be coated with or include materials to scatter the light. The diffuser 176 can have a surface configured to scatter light, for example frosting or roughness.

Optionally, the phosphor 178 can be included in the smart light bulb 162. The phosphor 178 is a phosphor excited by light of one wavelength and emitting light of another wavelength. In an embodiment, the phosphor 178 is a phosphor excited by UV light such as near UV light provided by the first LED 174*a*. In an embodiment, the phosphor 178 emits white light when it has been excited by the UV light. The light emitted by the phosphor can have any suitable color or color temperature for use in providing lighting. In an embodiment, the phosphor 178 absorbs approximately 30% or less of the UV light generated by the first LED 174*a*. In an embodiment, the phosphor 178 provides light having a color temperature that is between 2000 K and 6000 K. In an embodiment, the phosphor 178 provides light having a color temperature between 3000 K and 6000 K. In an embodiment, the phosphor 178 is applied as a coating to a surface of the diffuser 176. In an embodiment, the phosphor 178 is applied as a coating to an inner surface of the diffuser 176 facing the LEDs of the smart light bulb 162. In an embodiment, the phosphor 178 is incorporated into the diffuser 176, for example with particles of the phosphor 178 being distributed in the material used to form the diffuser 176. In another embodiment, the phosphor 178 can be provided as a coating on the first LED 174*a*, the second LED 174*b* and/or any of the other LEDs 174*c-n* included in the smart light bulb 162. In another embodiment, the phosphor 178 can be included in a material positioned between one or more of the LEDs 174*a-n* and the diffuser 176.

Optionally, a UV camera 180 can be included in the smart light bulb 162. The UV camera 180 can capture images of at least a portion of the space in which the bulb 162 is located. The image captured by the UV camera 180 can be sent to another device such as the remote device 164 or the server 166 to be processed, for example to estimate amounts of pathogens within the space by detecting fluorescence of those pathogens following exposure to suitable UV light. The image(s) captured by the UV camera 180 can be sent to the remote device 164 or the server 166 using the wireless communication antenna 170. In an embodiment, the UV camera 180 is powered by power received by the smart light bulb 162 at the screw-thread base 168.

In an embodiments, the smart lighting system 160 can include multiple ones of the smart light bulbs 162. Each of these multiple smart light bulbs 162 can be individually addressable and/or assigned to groups such that control signals can be specific to particular smart light bulbs 162 or groups thereof that are included within the smart lighting system 160.

The remote device 164 is a device separate from the smart light bulb 162 and not connected to the electrical circuit supplying power to the screw-thread base 168 of the smart light bulb 162. The remote device 164 includes a processor 182 and a wireless communication transmitter 184. The remote device 164 can be any suitable device including the processor 182 and the wireless communication transmitter 184, with non-limiting examples of such remote devices including but not limited to mobile phones, tablets, digital home assistants, remote controls, or the like. The remote device 164 can further include data storage 185. The data storage 185 can include, for example, storage of operation instructions, data received from the wireless communication transmitter 184.

The processor 182 of the remote device 164 is configured to determine operation of the smart light bulb 162. Determination of the operation of the smart light bulb 162 can be based on user input, such as a voice command or other input collected from an optional user input device 186 such as a microphone, keyboard, mouse, touch screen, or the like. The determination of operation by the processor 182 can be based on a schedule and/or a profile of user behavior and/or preferences dictating particular lighting conditions for particular times and/or based on other events or conditions. In embodiments where the smart lighting system 160 includes multiple smart light bulbs 162, the determined operation can include the selection of one or more smart light bulbs 162 in the smart lighting system to carry out particular operations. In an embodiment, the determination of operation can be based on a period over which to irradiate a space with ultraviolet (UV) light using one or more of the smart light bulbs. The determination of operation can include a command for the smart light bulb to provide UV light if there has not been sufficient UV irradiation of a space where the smart light bulb is located during a predetermined period of time. The period to irradiate the space with UV light can be based on, for example, fixed values for recommended UV exposure to inactivate pathogens in a space, or determined based on measurements such as amounts of pathogens in the space, totals of detected UV irradiation within the space during the predetermined period of time, or the like. The processor 182 can generate a control signal to be sent by the wireless communication transmitter 184 instructing the smart light bulb 162 to operate according to the operations determined at the processor 182.

The wireless communication transmitter 184 of the remote device 164 is a transmitter configured to transmit the control signal generated by the processor 182. The wireless communication transmitter 184 can be any suitable transmitter for wireless communication with the wireless communication antenna 170 of the smart light bulb 162. The wireless communication transmitter 184 can be a transmitter for any wireless communication protocol the wireless communication antenna is configured to be operable with, non-limiting examples including Bluetooth, ZigBee, Wi-Fi, any 802.11 protocols, or near-field communications.

In embodiments, the smart lighting system 160 can include multiple remote devices such as the remote device 164. The multiple remote devices can be different kinds of remote devices, such as a digital home assistant and one or more mobile phones or tablets. Each of the remote devices can be capable of sending control signals to any smart light bulbs included in the smart lighting system 160.

In an embodiment, the smart lighting system further includes the server 166. The server 166 is a server separate from the remote device 164 and the smart light bulb 162. The server 166 is configured to receive data from at least one of the remote device 164 and the smart light bulb 162. The server 166 can be at a remote location, separate from the location including the space illuminated by the smart light bulb 162. The server 166 can be a cloud server. The server 166 is configured to perform at least some data processing functions for the smart lighting. In an embodiment, the server 166 can, alone or in combination with the remote device 164, determine operation of the smart lighting system. In an embodiment, the server 166 can process data from the UV camera 180 to estimate levels of pathogens based on their fluorescence. In an embodiment, the data from the UV camera 180 can be obtained from the smart light bulb 162 or the remote device 164. In an embodiment, the server 166 can receive pathogen level information from a testing device 167. The testing device 167 can be any suitable device separate from the smart light bulb 162 capable of measuring pathogens in the space. The testing device 167 can be any suitable detector for detecting one or more pathogens of interest. In an embodiment, the testing device 167 can be a device using electromagnetic energy to detect the pathogen. Non-limiting examples of uses of electromagnetic energy to detect pathogens and testing devices for detecting pathogens can be found in U.S. Pat. Nos. 7,996,173, 8,076,630, 8,081,304, 8,285,510, 8,368,878, 8,583,394, 8,888,207, 8,988,666, 9,041,920, 9,316,581, 9,625,371, 9,664,610, and 9,869,636, which are herein incorporated by reference. In an embodiment, the server 166 is further configured to determine effectiveness of disinfection based on the levels of pathogens and the previous applications of UV light to the space. The effectiveness of disinfection can further be used as feedback to adjust the provision of UV light to the space by the smart lighting system 160, for example increasing the duration of providing the UV light if the effectiveness of disinfection falls below acceptable or desired levels. In an embodiment, the effectiveness of disinfection can be used to prepare a report for a user, for example accessible by an application, a website, or viewable on the remote device 164.

Figure 18:
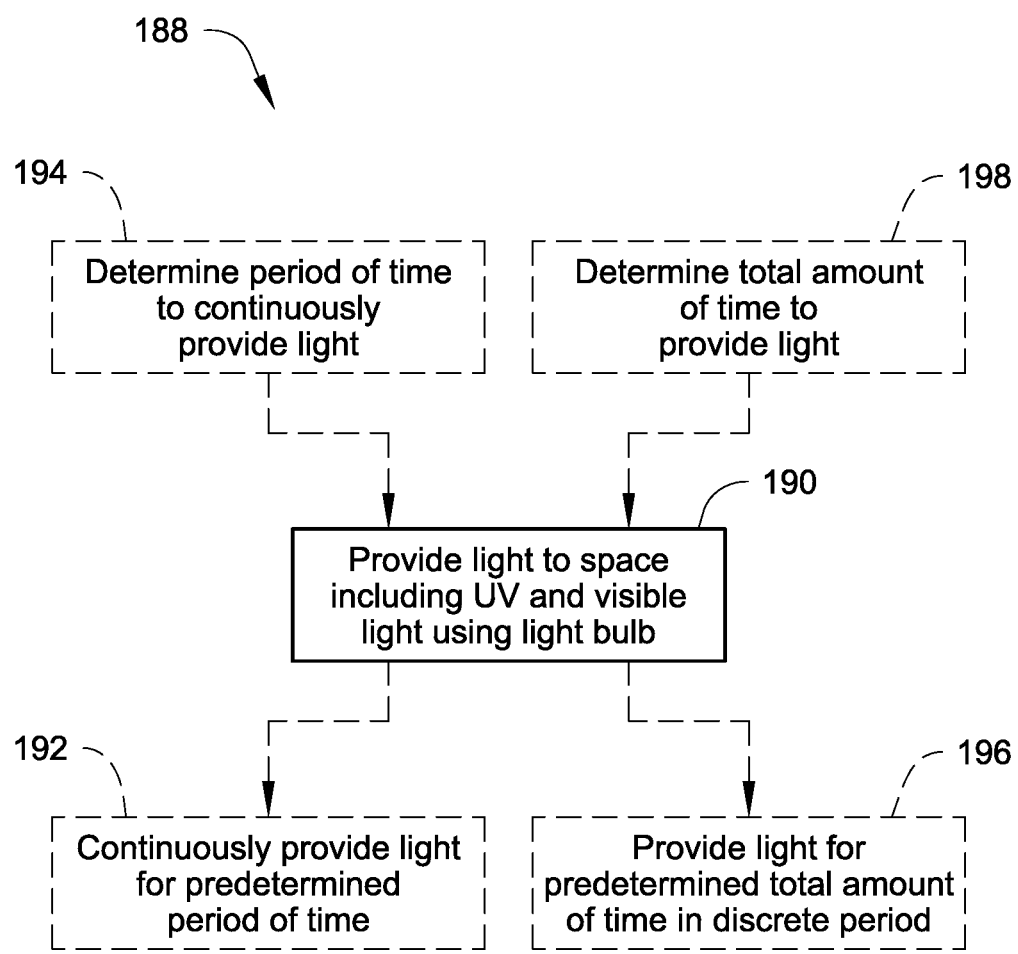
FIG. 18 shows a method of providing light to a space for disinfecting the space.

FIG. 18 shows a method 188 of providing light to a space that can disinfect the space. The method 188 includes, in step 190, providing light to the space using a consumable and replaceable light bulb, with the light including ultraviolet (UV) light and visible light. The light bulb can replace a preexisting light bulb in a preexisting fixture to provide disinfection without removing or altering existing fixtures. Optionally, the method 188 can include, in step 192, providing the UV and visible light to the space for at least a predetermined period of time. Optionally, the method 188 can also include, in step 194, determining the predetermined period of time. Optionally, the method 188 can include, in step 196, providing the UV and visible light to the space for at least a predetermined total amount of time within a discrete time period. Optionally, the method 188 can include, in step 198, determining the predetermined total amount of time.

The light bulb used in the method 188 can be any light bulb described herein capable of providing UV light and visible light, such as light bulbs 10, 50, 100, 160 shown in FIGS. 1-17. Providing light to the space using the light bulb includes providing power to the light bulb. When the light bulb is a smart light bulb, providing light can further include the smart light bulb providing power to at least one LED included therein based on a control signal.

The UV light provided is UV light within a range of wavelengths deemed safe for human exposure. The UV light can have a wavelength of between 200 nm and 405 nm. In an embodiment, the UV light has a wavelength of between 200 nm and 395 nm. In an embodiment, the UV light has a wavelength of between 380 nm and 395 nm. In an embodiment, the light bulb produces the UV light by excitation of a phosphor using visible light output by one or more LEDs included in the light bulb. The phosphor can be, for example, provided as a coating on a diffuser of the light bulb, included in the diffuser of the light bulb, or provided on a surface of at least one of the one or more LEDs. In another embodiment, the UV light does not excite a phosphor, and white light is instead provided from other LEDs in the light bulb, for example as described with respect to FIGS. 1-9, or the white light is generated from the UV light combining with light emitted by one or more additional LEDs.

The visible light provided can be any suitable visible light for illuminating the space. In an embodiment, the visible light is white light. In an embodiment, the visible light can have a color temperature suitable for use in ambient lighting, such as a soft white, a cool white, a warm white, a bright white, or a daylight color temperature. The visible light can be colored (i.e. non-white) light. The visible light can be provided by one or more LEDs included in the light bulb. In an embodiment, color of the visible light can be controlled (i.e. selected or varied) by controlling the relative intensity of light produced by different LEDs within the light bulb, these LEDs each providing different colors of light. In an embodiment, the visible light can be generated by a phosphor included in the light bulb. In an embodiment, the visible light can be white light resulting from a combination of yellow light produced by the light bulb combined with the UV light. Optionally, the light bulb can also be operated to provide only one of the visible light or the UV light. Optionally, the operation to provide one or both of the visible light and the UV light can be selected at the light bulb, for example by way of a toggle switch included on the light bulb. In an embodiment, the operation to provide one or both of the visible light and the UV light can be selected by using a switch controlling power to the light bulb, such as by operating the switch according to a predetermined pattern.

Optionally, the method 188 can include providing the light to provide sufficient UV irradiation to the space to achieve a desired effectiveness for inactivating pathogens. Inactivation of pathogens by UV light is a function of the wavelength of the light, its intensity, and the duration of the irradiation, with longer times increasing the proportion of pathogens inactivated by the irradiation. The wavelength and intensity can be constrained by the properties and power of the light bulb, such as the wavelength of UV light provided by the phosphor and the lumen rating of the LEDs within the light bulb. The duration of exposure can be controlled separately from the wavelength and intensity and can be used to affect the effectiveness of the light in inactivating pathogens in the space.

In an embodiment, the method 188 can include continuously providing the UV and visible light to the space for at least a predetermined period of time. The light can be provided continuously by, for example, using a timer to control when the light can be turned off. The predetermined period of time can be a fixed period of time selected based on data regarding pathogen inactivation by the UV light, for example a period of time needed to achieve 95%, 99%, or 99.9% inactivation of pathogens in a sample. In an embodiment, the method can also include determining the predetermined period of time for which the UV light is provided to the space. The predetermined period of time can be determined based on an estimate or measure of pathogens within the space, a time since the last use of the light bulb to light the space, or any other suitable determination of the approximate level of pathogens in the space and UV exposure suitable to disinfect the space under such conditions. In an embodiment, the measure of pathogens can be a measurement based on UV camera imaging of the space. In an embodiment, the measurement based on UV camera imaging of the space can include irradiation of the space with UV at a wavelength selected to cause fluorescence in the pathogens. In an embodiment, the irradiation of the space with UV can be provided by the light bulb used to provide visible and UV light.

In an embodiment, the method 188 can include providing the UV and visible light to the space for at least a predetermined total amount of time within a discrete time period. The discrete period can be a pre-set time period for regular disinfection of the space. In an embodiment, providing the light for the total amount of time within the discrete time period can include activating the light bulb to provide the light based on a remaining amount of the discrete time period, a current time, and a remaining amount of time to provide the light during the discrete time period, such that the light is activated at times to ensure that it is operated for the total amount of time before the end of the discrete time period. The total amount of time can be a total amount of UV irradiation needed over the discrete time period to achieve a desired level of pathogen inactivation within that discrete time period. The total amount of time can be a fixed amount of time. The fixed amount of time can be based, for example, on the time needed to achieve 95%, 99%, or 99.9% inactivation of pathogens in a sample. In an embodiment, the method 188 can further include determining the predetermined total amount of time. The predetermined total amount of time can be determined based on an estimate or measure of pathogens within the space, a time since the last use of the light bulb to light the space, or any other suitable determination of the approximate level of pathogens in the space and UV exposure suitable to disinfect the space under such conditions. In an embodiment, the measure of pathogens can be a measurement based on UV camera imaging of the space. In an embodiment, the measurement based on UV camera imaging of the space can include irradiation of the space with UV at a wavelength selected to cause fluorescence in the pathogens. In an embodiment, the irradiation of the space with UV can be provided by the light bulb used to provide visible and UV light.

Figure 19:
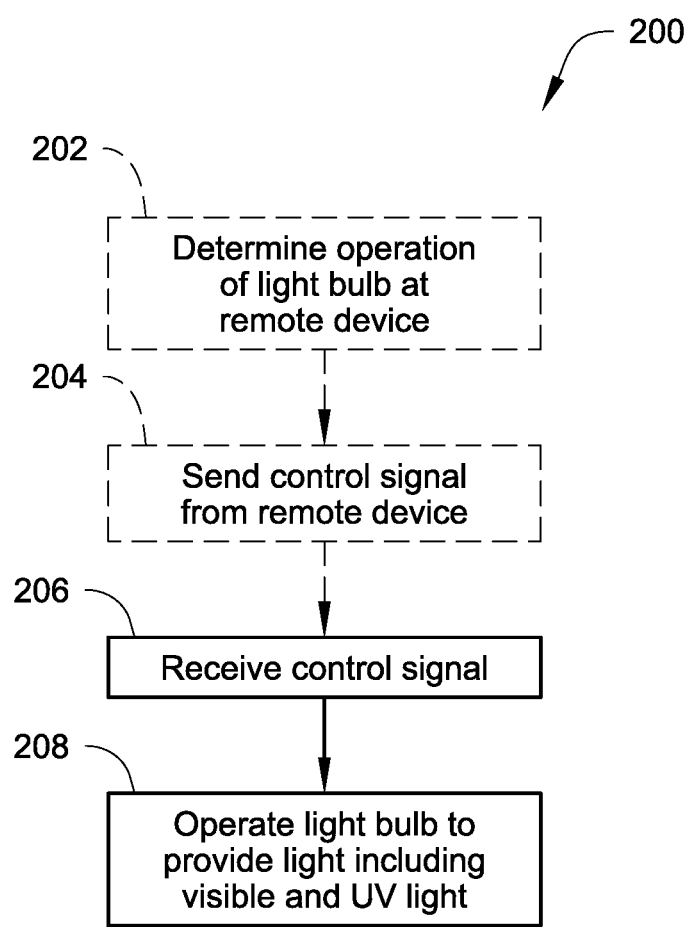
FIG. 19 shows a flow chart of a method of controlling a smart bulb according to an embodiment.

FIG. 19 shows a flow chart of a method 200 of controlling a smart bulb according to an embodiment. The method 200 includes determining operation of the light bulb at a remote device in a step 202, sending a control signal from the remote device in a step 204, receiving the control signal at the light bulb in step 206, and operating the light bulb according to the control signal at step 208.

Operation of the light bulb is determined at a remote device at step 202. The determination of operation can be a determination of whether to turn the light bulb on or off or to vary a parameter of the light being supplied by the light bulb, such as an intensity and/or color of light to be provided. The determination of operation can be based on user input, such as a voice command or input collected from an input device such as a microphone, keyboard, mouse, touch screen, or the like. The determination of operation can be based on a schedule and/or a profile of user behavior and/or preferences dictating particular lighting conditions for particular times and/or based on other events or conditions. In embodiments where the smart lighting system includes multiple smart light bulbs, the operation of the smart light bulb at step 208 can include the selection of one or more smart light bulbs in the smart lighting system to carry out particular operations. In an embodiment, the determination of operation can be based on a period over which to irradiate a space with ultraviolet (UV) light using one or more of the smart light bulbs. The determination of operation can include a command for the smart light bulb to provide UV light if there has not been sufficient UV irradiation of a space where the smart light bulb is located during a predetermined period of time. The period to irradiate the space with UV light can be based on, for example, fixed values for recommended UV exposure to inactivate pathogens in a space, or determined based on measurements such as amounts of pathogens in the space, totals of detected UV irradiation within the space during the predetermined period of time, or the like.

A control signal is sent by the remote device at step 204. The control signal includes a command to operate the light bulb according to the operation determined at step 202. The control signal can include the operation to be carried out, such as turning the light on, turning the light off, increasing or decreasing the intensity of the light, or changing the relative intensity of various wavelengths to change a color of the light. The control signal can optionally further include a time or times at which to carry out the operation, a rate of change for changes to the intensity of the light or particular wavelengths, or any other suitable modifiers or scheduling for the operations to be carried out. The control signal can be sent by any suitable wireless communications method receivable at one or more smart light bulbs, with non-limiting examples of such wireless communications including Bluetooth, ZigBee, Wi-Fi, any 802.11 protocols, or near-field communications. In embodiments including multiple smart light bulbs, the control signal sent by the remote device at step 204 may include identifiers for which smart light bulbs or groups of smart light bulbs are to respond to the control signal.

The control signal is received at the smart light bulb at step 206. The control signal is received at 206 using a wireless communications antenna included in the smart light bulb. The wireless communications antenna is configured to receive wireless communications from the remote device. The wireless communications can be according to any suitable wireless communication method, with non-limiting examples of such wireless communications including Bluetooth, ZigBee, Wi-Fi, any 802.11 protocols, or near-field communications.

The smart light bulb is operated according to the control signal at step 208. Operation of the light bulb includes control of the supply of power to one or more LEDs included in the smart light bulb based on the control signal received at step 206. When at least one of the LEDs included in the smart light bulb are powered, the smart light bulb can emit both visible light and UV light, with the UV light being within a range of wavelengths deemed safe for human exposure. In an embodiment, the UV light can have a wavelength between 200 nm and 405 nm. In an embodiment, the UV light can have a wavelength between 200 nm and 395 nm. In an embodiment, the UV light can have a wavelength between 380 nm and 395 nm.

When the smart light bulb provides UV light when operated according to the control signal at step 208, the UV light irradiates surfaces exposed to this light. UV irradiation at these frequencies can lead to the inactivation of pathogens, including inhibition of reproduction of bacteria or viruses, rendering viruses inactive, or killing bacteria. The extent of inactivation of pathogens can be dependent on time of exposure to the UV light. In embodiments, operating the smart light bulb according to the control signal at step 208 can include providing the UV light for at least a predetermined amount of time based on the effectiveness of that level of exposure in inactivating pathogens.

Figure 20:
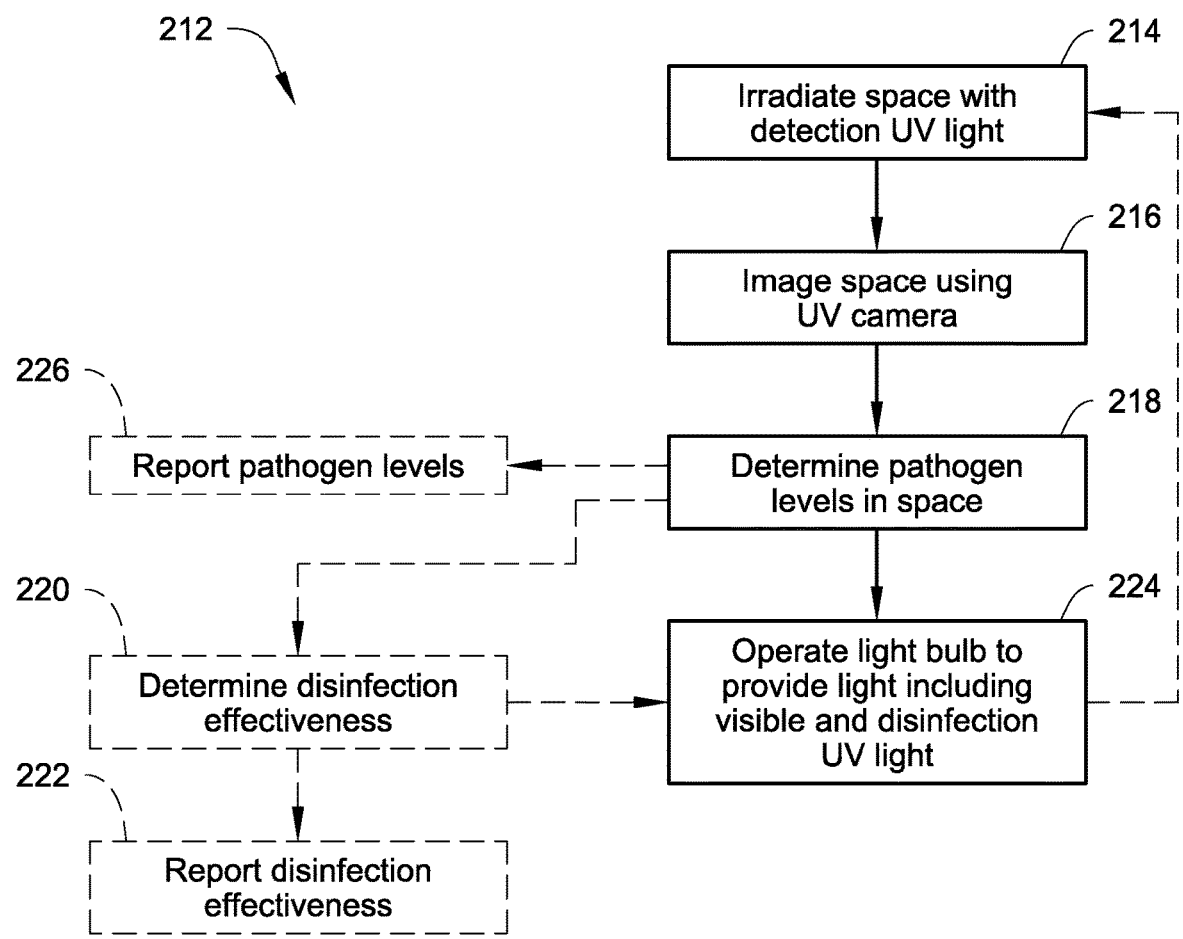
FIG. 20 shows a flow chart of a method of detecting pathogens in a space and controlling a smart bulb according to an embodiment.

FIG. 20 shows a flow chart of a method 212 of detecting pathogens in a space and controlling a smart bulb according to an embodiment. The method 212 includes irradiating a space with a detection UV light at step 214, imaging the space using a UV camera at step 216, and determining pathogen levels in the space at step 218. The method 212 can further include determining disinfection effectiveness at step 220 and reporting the disinfection effectiveness at step 222. A light bulb is operated to provide visible light and disinfection UV light to the space at step 224.

A space where pathogens are to be detected is irradiated with a detection UV light at step 214. The detection UV light can be UV light that includes a wavelength that causes fluorescence in at least some pathogens of interest. The pathogens can be any bacteria or viruses such as the examples provided above. In an embodiment, the wavelength of the detection UV light has a wavelength that is between 240 nm and 350 nm. In an embodiment, the detection UV light is provided by an LED included in at least one light bulb used in a lighting system included in carrying out the method 212. In an embodiment, the detection UV light is provided by another device such as, for example, a testing device or any other controllable source of UV light having proper wavelength to be used as the detection UV light.

The space is then imaged using a UV camera at step 216. Imaging with the UV camera captures fluorescence of pathogens in the space that were irradiated with the detection UV light at step 214. The UV camera can be any suitable detector that can capture an image including light in the UV range of the spectrum. In an embodiment, the UV camera is part of a testing device or kit. In an embodiment, the UV camera is included in at least one light bulb included in a smart lighting system that carries out at least a portion of method 212. In an embodiment, the UV camera is part of a security or monitoring system for the space that is imaged at step 216. In an embodiment, the UV camera is included in a mobile device such as a phone or a tablet.

Pathogen levels in the space are determined at step 218. The pathogens can be any pathogens identified above that fluoresce when irradiated with the detection UV light. The pathogen levels can be determined by processing the image captured by the UV camera at step 216 to determine the levels of the pathogens based on their fluorescence following the irradiation with the detection UV light at step 214. The intensity of UV light resulting from fluorescence can be used to determine pathogen levels on surfaces in the space included in the images captured by the UV camera. In an embodiment, the determination of pathogen levels is performed at a remote device included in a smart lighting system. In an embodiment, the determination of pathogen levels is performed at a server, such as a cloud server. In an embodiment, the determination of pathogen levels is performed at a digital home assistant. In an embodiment, the determination of pathogen levels is performed on a mobile device such as a smart phone or tablet computer.

In another embodiment, determination of pathogen levels at step 218 in the space can be performed without providing UV light detection at step 214 or imaging using a UV camera at step 216. In an embodiment, a testing device separate from the light bulb can be used to determine the pathogen levels step 218. The testing device can be any suitable detector for detecting one or more pathogens of interest. In an embodiment, the testing device can be a device using electromagnetic energy to detect the pathogen. Non-limiting examples of uses of electromagnetic energy to detect the pathogen and testing devices for detecting the pathogen can be found in U.S. Pat. Nos. 7,996,173, 8,076,630, 8,081,304, 8,285,510, 8,368,878, 8,583,394, 8,888,207, 8,988,666, 9,041,920, 9,316,581, 9,625,371, 9,664,610, and 9,869,636, which are herein incorporated by reference.

In an embodiment, the pathogen levels can be reported to a user at step 226. The pathogen levels can be reported to the user by way of a display. The display can be a display included in, for example, a computer, smart phone, or tablet computer accessing a website or using an application to obtain the reported pathogen levels. In an embodiment, the display is a display included in a digital home assistant. In an embodiment, the pathogen levels are reported at the same device where pathogen levels are determined at step 218. In an embodiment, the pathogen levels are reported at a device separate from the device where the pathogen levels are determined at step 218. In an embodiment, the pathogen levels are sent from a device where they are determined to the device including the display where the pathogen levels are reported.

A light bulb is operated to provide visible light and disinfection UV light to the space at step 224. The visible light and the disinfection UV light are provided to the space at the same time when the light bulb is operated. The visible light can be ambient lighting for the space. The disinfection UV light is UV light having a wavelength and intensity that are safe for human exposure while remaining capable of inactivating pathogens. The disinfection UV light can have a wavelength of between 200 nm and 405 nm. In an embodiment, the disinfection UV light has a wavelength of between 200 nm and 395 nm. In an embodiment, the disinfection UV light has a wavelength of between 380 and 395 nm. The light bulb can be any suitable light bulb providing both visible light and disinfection UV light, such as any of the light bulbs disclosed herein. In an embodiment, the duration that the light bulb is operated at step 224 is based on the pathogen levels determined at step 218.

The method 212 can further include determining disinfection effectiveness at step 220. Disinfection effectiveness can be determined using historical data regarding the pathogen levels in the space and treatment information regarding the use of disinfection UV light. This historical data can be captured over iterations of the method 212. The disinfection effectiveness can include, for example, correlations between times during which the disinfection UV light is provided to the space and the pathogen levels or changes in the pathogen levels that are observed in the space in subsequent determinations of pathogen levels. In an embodiment, the disinfection effectiveness determined at step 220 can be used as feedback for determining operation of the light bulb at step 224, for example increasing the duration of the operation of the light bulb if disinfection effectiveness is below an expected or desired level. The disinfection effectiveness can be determined at step 220 at the same device dictating operation of the light bulb at step 224 or at a separate device that reports the disinfection effectiveness to the device dictating operation of the light bulb at step 224. For example, disinfection effectiveness can be determined at a server, while a remote device such as a digital home assistant controls the operation of the light bulb.

The disinfection effectiveness determined at step 220 can be reported to a user at step 222. The disinfection effectiveness can be reported to the user by way of a display. The display can be a display included in, for example, a computer, smart phone, or tablet computer accessing a website or using an application to obtain the reported pathogen levels. In an embodiment, the display is a display included in a digital home assistant. In an embodiment, the disinfection effectiveness is reported at step 222 at the same device where disinfection effectiveness is determined at step 220. In an embodiment, the disinfection effectiveness is reported at a device separate from the device where the disinfection effectiveness is determined at step 220. In an embodiment, the disinfection effectiveness is sent from a device where they are determined to the device including the display where the pathogen levels are reported.

Additional embodiments can include the following:

Embodiment 1: A method of disinfecting a space can include replacing a consumable, replaceable light emitting device in a preexisting fixture in the space with a disinfecting consumable, replaceable light emitting device; and providing light to the space using the disinfecting consumable, replaceable light emitting device for at least a predetermined amount of time, wherein the light provided by the disinfecting light bulb including visible light and ultraviolet light having a wavelength between 200 nm and 395 nm.

Embodiment 2: The method of embodiment 1, wherein the predetermined amount of time is at least 10 minutes.

Embodiment 3: The method of embodiment 1, wherein the predetermined amount of time is within a range from one to four hours.

Embodiment 4: The method of embodiment 1, further comprising irradiating the space with a detection UV light and imaging the space using a UV camera, wherein the disinfecting consumable, replaceable light emitting device includes the UV camera.

Embodiment 5: The method of embodiment 4, wherein the detection UV light has a wavelength that is between 240 nm and 350 nm.

Embodiment 6: The method of embodiment 4, further comprising processing an image obtained in the imaging of the space using the UV camera to determine a pathogen level.

Embodiment 7: The method of embodiment 6, wherein the processing of the image is performed by a processor at a remote device, separate from the consumable, replaceable light emitting device.

Embodiment 8: The method of embodiment 6, wherein the processing of the image is performed by a processor at a server, the server at a location separate from a location including the space.

Embodiment 9: The method of embodiment 6, further comprising determining a disinfection effectiveness based on the pathogen levels, and wherein determining the disinfection effectiveness based on the pathogen levels is performed at a remote device, separate from the consumable, replaceable light emitting device.

Embodiment 10: The method of embodiment 6, further comprising determining a disinfection effectiveness based on the pathogen levels, and wherein determining the disinfection effectiveness based on the pathogen levels is performed by a processor at a server, the server at a location separate from a location including the space.

Embodiment 11: A method of controlling a light bulb can include determining operation of the light bulb at a remote device; sending a control signal from the remote device to the light bulb, the control signal directing the determined operation of the light bulb; receiving the control signal at a wireless communication antenna included in the light bulb; operating the light bulb according to the control signal, wherein the remote device is separate from the light bulb; and operating the light bulb includes providing visible light and providing ultraviolet (UV) light having a wavelength of between 200 nm to 395 nm.

Embodiment 12: The method of embodiment 11, wherein the light bulb includes a plurality of light emitting diodes (LEDs), at least one of the LEDs emits the UV light, and operating the light bulb includes controlling a relative amount of light emitted from each of the plurality of LEDs.

Embodiment 13: The method of embodiment 11, further comprising imaging the space using a UV camera included in the light bulb.

Embodiment 14: The method of embodiment 13, further comprising sending an image of the space captured during the imaging of the space using the UV camera from the light bulb to the remote device.

Embodiment 15: The method of embodiment 14, further comprising processing the image of the space at the remote device to determine a pathogen level.

Embodiment 16: The method of embodiment 15, further comprising transmitting the image of the space from the remote device to a server, separate from the remote device; and processing the image of the space at the server to determine a pathogen level.

Embodiment 17: The method of embodiment 13, wherein imaging the space using the UV camera is performed while a light emitting diode of the light bulb emits UV light having a wavelength between 240 nm and 350 nm.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A light bulb, comprising:
a housing;
a screw-thread base attached to the housing for threading the light bulb into a threaded socket;
the housing defining an interior space;
white light emitting diodes in the interior space, the white light emitting diodes are capable of emitting white light;
blue light emitting diodes in the interior space, the blue light emitting diodes are capable of emitting ultraviolet (UV) light;
a visible wavelength filter positioned relative to the blue light emitting diodes to filter out visible wavelengths of the UV light emitted by any one or more of the blue light emitting diodes,
wherein the visible wavelength filter has a black color, and the visible wavelength filter is centrally positioned at an end of the housing opposite the screw-thread base.

2. The light bulb of claim 1, wherein the UV light has a nominal wavelength of about 365 nm.

3. The light bulb of claim 1, wherein the UV light has a nominal wavelength of about 320 nm.

4. The light bulb of claim 1, further comprising a UV light indicator that is visible externally of the light bulb that indicates operation of any one or more of the blue light emitting diodes.

5. The light bulb of claim 1, further comprising a partition that separates white light emitted by the white light emitting diodes from UV light emitted by the blue light emitting diodes.

6. The light bulb of claim 1, further comprising a distance sensor, and a controller operatively connected to the distance sensor and to the blue light emitting diodes, wherein the controller controls operation of the blue light emitting diodes based on a signal received from the distance sensor.

7. The light bulb of claim 1, further comprising a motion sensor, and a controller operatively connected to the motion sensor and to the blue light emitting diodes, wherein the controller controls operation of the blue light emitting diodes based on a signal received from the motion sensor.

8. The light bulb of claim 1, further comprising a power controller operatively connected to the blue light emitting diodes that controls a power level of the blue light emitting diodes.

9. The light bulb of claim 1, further comprising a distance sensor, a motion sensor, and a controller; the controller is operatively connected to the distance sensor, the motion sensor, the white light emitting diodes and to the blue light emitting diodes in a manner so that the light bulb can be controlled by the controller to operate in any operational mode of a set of operational modes, the set of operational modes comprising:
a first mode, wherein when no motion is detected by the motion sensor, both the blue light emitting diodes and the white light emitting diodes are on, when motion is sensed by the motion sensor, both the blue light emitting diodes and the white light emitting diodes are on, and wherein when a person is within a threshold range of the light bulb, the blue light emitting diodes are off and the while light emitting diodes are on;
a second mode, wherein when no motion is detected by the motion sensor, both the blue light emitting diodes and the white light emitting diodes are on, when motion is sensed by the motion sensor, the blue light emitting diodes are off and the white light emitting diodes are on, and wherein when a person is within a threshold range of the light bulb, the blue light emitting diodes are off and the while light emitting diodes are on;
a third mode, wherein when no motion is detected by the motion sensor, the blue light emitting diodes are on and the white light emitting diodes are off, when motion is sensed by the motion sensor, both the blue light emitting diodes and the white light emitting diodes are on, and wherein when a person is within a threshold range of the light bulb, the blue light emitting diodes are off and the while light emitting diodes are on; and
a fourth mode, wherein when no motion is detected by the motion sensor, the blue light emitting diodes are on and the white light emitting diodes are off, when motion is sensed by the motion sensor, the blue light emitting diodes are off and the white light emitting diodes are on, and wherein when a person is within a threshold range of the light bulb, the blue light emitting diodes are off and the while light emitting diodes are on.

10. A system comprising:
the light bulb of claim 1;
at least one device separate from and in wireless communication with the light bulb, the at least one device comprises one or more of the following:
a mobile phone; a digital assistant; a server; a UV camera; a pathogen sensor;
wherein operation of the white light emitting diodes and/or the blue light emitting diodes are controlled based on a signal received from the at least one device.

11. The system of claim 10, comprising a plurality of the light bulbs, and the at least one device is in wireless communication with each of the light bulbs.

12. A system comprising:
a plurality of the light bulbs of claim 1;
wherein the light bulbs are in direct or indirect wireless communication with each other.

13. The light bulb of claim 1, wherein all of the white light emitting diodes are disposed radially outwards of the visible wavelength filter.

14. The light bulb of claim 1, wherein the end of the housing opposite the screw-thread base is flat.

15. The light bulb of claim 1, further comprising a controller connected to and controlling operation of the blue light emitting diodes, and wherein the blue light emitting diodes are controlled by the controller in a manner so that the UV light emitted by the blue light emitting diodes inactivates COVID-19 virus by at least 99% at 6 hours of exposure to said UV light.

16. The light bulb of claim 1, further comprising a controller connected to and controlling operation of the blue light emitting diodes, and wherein the blue light emitting diodes are controlled by the controller in a manner so that the blue light emitting diodes provide a maximum effective irradiance of 30 J/m$^2$ or less over the course of 8 hours of continuous exposure.

17. The light bulb of claim 1, further comprising a controller connected to and controlling operation of the blue light emitting diodes, and wherein the controller is disposed between the screw-thread base and the blue light emitting diodes.

18. A light bulb, comprising:
a housing;
a screw-thread base attached to the housing for threading the light bulb into a threaded socket;
the housing defining an interior space;
white light emitting diodes in the interior space, the white light emitting diodes are capable of emitting white light;
blue light emitting diodes in the interior space, the blue light emitting diodes are capable of emitting ultraviolet (UV) light;
a visible wavelength filter positioned relative to the blue light emitting diodes to filter out visible wavelengths of the UV light emitted by any one or more of the blue light emitting diodes, wherein the visible wavelength filter has a black color, and the visible wavelength filter is centrally positioned at an end of the housing opposite the screw-thread base;
and the light bulb is devoid of phosphor through which UV light emitted by any one or more of the blue light emitting diodes passes for conditioning the UV light.

19. The light bulb of claim 18, wherein the UV light has a nominal wavelength of about 365 nm.

20. The light bulb of claim 18, wherein the UV light has a nominal wavelength of about 320 nm.

21. The light bulb of claim 18, further comprising a UV light indicator that is visible externally of the light bulb that indicates operation of any one or more of the blue light emitting diodes.

22. The light bulb of claim 18, further comprising a partition that separates white light emitted by the white light emitting diodes from UV light emitted by the blue light emitting diodes.

23. The light bulb of claim 18, further comprising a distance sensor, and a controller operatively connected to the distance sensor and to the blue light emitting diodes, wherein the controller controls operation of the blue light emitting diodes based on a signal received from the distance sensor.

24. The light bulb of claim 18, further comprising a motion sensor, and a controller operatively connected to the motion sensor and to the blue light emitting diodes, wherein the controller controls operation of the blue light emitting diodes based on a signal received from the motion sensor.

25. The light bulb of claim 18, further comprising a power controller operatively connected to the blue light emitting diodes that controls a power level of the blue light emitting diodes.

26. The light bulb of claim 18, further comprising a distance sensor, a motion sensor, and a controller; the controller is operatively connected to the distance sensor, the motion sensor, the white light emitting diodes and to the blue light emitting diodes in a manner so that the light bulb can be controlled by the controller to operate in any operational mode of a set of operational modes, the set of operational modes comprising:
a first mode, wherein when no motion is detected by the motion sensor, both the blue light emitting diodes and the white light emitting diodes are on, when motion is sensed by the motion sensor, both the blue light emitting diodes and the white light emitting diodes are on, and wherein when a person is within a threshold range of the light bulb, the blue light emitting diodes are off and the while light emitting diodes are on;
a second mode, wherein when no motion is detected by the motion sensor, both the blue light emitting diodes and the white light emitting diodes are on, when motion is sensed by the motion sensor, the blue light emitting diodes are off and the white light emitting diodes are on, and wherein when a person is within a threshold range of the light bulb, the blue light emitting diodes are off and the while light emitting diodes are on;
a third mode, wherein when no motion is detected by the motion sensor, the blue light emitting diodes are on and the white light emitting diodes are off, when motion is sensed by the motion sensor, both the blue light emitting diodes and the white light emitting diodes are on, and wherein when a person is within a threshold range of the light bulb, the blue light emitting diodes are off and the while light emitting diodes are on; and
a fourth mode, wherein when no motion is detected by the motion sensor, the blue light emitting diodes are on and the white light emitting diodes are off, when motion is sensed by the motion sensor, the blue light emitting diodes are off and the white light emitting diodes are on, and wherein when a person is within a threshold range of the light bulb, the blue light emitting diodes are off and the while light emitting diodes are on.

27. A system comprising:
the light bulb of claim 14;
at least one device separate from and in wireless communication with the light bulb, the at least one device comprises one or more of the following:
a mobile phone; a digital assistant; a server; a UV camera; a pathogen sensor;
wherein operation of the white light emitting diodes and/or the blue light emitting diodes are controlled based on a signal received from the at least one device.

28. The system of claim 27, comprising a plurality of the light bulbs, and the at least one device is in wireless communication with each of the light bulbs.

29. A system comprising:
a plurality of the light bulbs of claim 14;
wherein the light bulbs are in direct or indirect wireless communication with each other.

30. The light bulb of claim 18, wherein all of the white light emitting diodes are disposed radially outwards of the visible wavelength filter.

31. The light bulb of claim 18, wherein the end of the housing opposite the screw-thread base is flat.

32. The light bulb of claim 18, further comprising a controller connected to and controlling operation of the blue light emitting diodes, and wherein the blue light emitting diodes are controlled by the controller in a manner so that the UV light emitted by the blue light emitting diodes inactivates COVID-19 virus by at least 99% at 6 hours of exposure to said UV light.

33. The light bulb of claim 18, further comprising a controller connected to and controlling operation of the blue light emitting diodes, and wherein the blue light emitting diodes are controlled by the controller in a manner so that the blue light emitting diodes provide a maximum effective irradiance of 30 $J/m^2$ or less over the course of 8 hours of continuous exposure.

34. The light bulb of claim 18, further comprising a controller connected to and controlling operation of the blue light emitting diodes, and wherein the controller is disposed between the screw-thread base and the blue light emitting diodes.

35. A light bulb, comprising:
a housing;
a screw-thread base attached to the housing for threading the light bulb into a threaded socket;
the housing defining an interior space;
white light emitting diodes in the interior space, the white light emitting diodes are capable of emitting white light;
blue light emitting diodes in the interior space, the blue light emitting diodes are capable of emitting ultraviolet (UV) light;
a visible wavelength filter positioned relative to the blue light emitting diodes to filter out visible wavelengths of the UV light emitted by any one or more of the blue light emitting diodes, wherein the visible wavelength filter has a black color, and the visible wavelength filter is centrally positioned at an end of the housing opposite the screw-thread base;
a distance sensor;
a motion sensor; and
a controller, wherein the controller is operatively connected to the distance sensor, the motion sensor, the white light emitting diodes and to the blue light emitting diodes in a manner so that the light bulb can be controlled by the controller to operate in any operational mode of a set of operational modes comprising:
a first mode, wherein when no motion is detected by the motion sensor, both the blue light emitting diodes and the white light emitting diodes are on, when motion is sensed by the motion sensor, both the blue light emitting diodes and the white light emitting diodes are on, and wherein when a person is within a threshold range of the light bulb, the blue light emitting diodes are off and the while light emitting diodes are on;
a second mode, wherein when no motion is detected by the motion sensor, both the blue light emitting diodes and the white light emitting diodes are on, when motion is sensed by the motion sensor, the blue light emitting diodes are off and the white light emitting diodes are on, and wherein when a person is within a threshold range of the light bulb, the blue light emitting diodes are off and the while light emitting diodes are on;
a third mode, wherein when no motion is detected by the motion sensor, the blue light emitting diodes are on and the white light emitting diodes are off, when motion is sensed by the motion sensor, both the blue light emitting diodes and the white light emitting diodes are on, and wherein when a person is within a threshold range of the light bulb, the blue light emitting diodes are off and the while light emitting diodes are on; and
a fourth mode, wherein when no motion is detected by the motion sensor, the blue light emitting diodes are on and the white light emitting diodes are off, when motion is sensed by the motion sensor, the blue light emitting diodes are off and the white light emitting diodes are on, and wherein when a person is within a threshold range of the light bulb, the blue light emitting diodes are off and the while light emitting diodes are on.

36. The light bulb of claim 35, wherein the UV light has a nominal wavelength of about 365 nm.

37. The light bulb of claim 35, wherein the UV light has a nominal wavelength of about 320 nm.

38. The light bulb of claim 35, further comprising a UV light indicator that is visible externally of the light bulb that indicates operation of any one or more of the blue light emitting diodes.

39. The light bulb of claim 35, further comprising a partition that separates white light emitted by the white light emitting diodes from UV light emitted by the blue light emitting diodes.

40. The light bulb of claim 35, further comprising a power controller operatively connected to the blue light emitting diodes that controls a power level of the blue light emitting diodes.

41. The light bulb of claim 35, wherein all of the white light emitting diodes are disposed radially outwards of the visible wavelength filter.

42. The light bulb of claim 35, wherein the end of the housing opposite the screw-thread base is flat.

43. The light bulb of claim 35, wherein the blue light emitting diodes are controlled by the controller in a manner so that the UV light emitted by the blue light emitting diodes inactivates COVID-19 virus by at least 99% at 6 hours of exposure to said UV light.

44. The light bulb of claim 35, wherein the blue light emitting diodes are controlled by the controller in a manner so that the blue light emitting diodes provide a maximum effective irradiance of 30 J/m$^2$ or less over the course of 8 hours of continuous exposure.

45. The light bulb of claim 35, wherein the controller is disposed between the screw-thread base and the blue light emitting diodes.

* * * * *